US008471085B2

(12) United States Patent
Sydora

(10) Patent No.: US 8,471,085 B2
(45) Date of Patent: Jun. 25, 2013

(54) OLIGOMERIZATION CATALYST SYSTEM AND PROCESS FOR OLIGOMERIZING OLEFINS

(75) Inventor: Orson L. Sydora, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 281 days.

(21) Appl. No.: 12/771,122

(22) Filed: Apr. 30, 2010

(65) Prior Publication Data

US 2010/0274065 A1 Oct. 28, 2010

Related U.S. Application Data

(63) Continuation-in-part of application No. 12/609,272, filed on Oct. 30, 2009.

(60) Provisional application No. 61/110,396, filed on Oct. 31, 2008, provisional application No. 61/110,407, filed on Oct. 31, 2008, provisional application No. 61/110,476, filed on Oct. 31, 2008.

(51) Int. Cl.
  *C07C 2/24* (2006.01)
  *C07C 2/02* (2006.01)
  *B01J 31/14* (2006.01)

(52) U.S. Cl.
  USPC .......... 585/513; 502/102; 502/103; 502/256; 502/167; 502/123; 585/604

(58) Field of Classification Search
  None
  See application file for complete search history.

(56) References Cited

U.S. PATENT DOCUMENTS

| 2,935,495 | A | 5/1960 | Kennedy |
| 3,100,764 | A | 8/1963 | Jezl et al. |
| 3,231,550 | A | 1/1966 | Manyik et al. |
| 3,242,099 | A | 3/1966 | Manyik et al. |
| 3,300,458 | A | 1/1967 | Manyik et al. |
| 3,347,840 | A | 10/1967 | Manyik et al. |
| 3,534,006 | A | 10/1970 | Kamaishi et al. |
| 3,558,676 | A | 1/1971 | Doherty et al. |
| 3,635,869 | A | 1/1972 | Steele et al. |
| 3,819,746 | A | 6/1974 | Katzakian, Jr. et al. |

(Continued)

FOREIGN PATENT DOCUMENTS

| CA | 2087578 | 7/1994 |
| CN | 1256968 | 6/2000 |

(Continued)

OTHER PUBLICATIONS

International Application PCT/2001/033431 Search Report dated Jun. 22, 2011.

(Continued)

*Primary Examiner* — Yun Qian
(74) *Attorney, Agent, or Firm* — Merchant & Gould P.C.

(57) ABSTRACT

Among other things, this disclosure provides an olefin oligomerization system and process, the system comprising: a) a transition metal compound; b) a pyrrole compound having a hydrogen atom on at the 5-position or the 2- and 5-position of a pyrrole compound and having a bulky substituent located on each carbon atom adjacent to the carbon atom bearing a hydrogen atom at the 5-position or the 2- and 5-position of a pyrrole compound. These catalyst system have significantly improved productivities, selectivities to 1-hexene, and provides higher purity 1-hexene within the $C_6$ fraction than catalyst systems using 2,4-dimethyl pyrrole.

28 Claims, 2 Drawing Sheets

U.S. PATENT DOCUMENTS

| | | |
|---|---|---|
| 3,838,101 A | 9/1974 | Steele et al. |
| 3,873,602 A | 3/1975 | Katzakian, Jr. et al. |
| 3,932,285 A | 1/1976 | Ceprini et al. |
| 3,962,182 A | 6/1976 | Steele et al. |
| 3,968,135 A | 7/1976 | Steele et al. |
| 3,977,996 A | 8/1976 | Katzakian, Jr. et al. |
| 3,978,026 A | 8/1976 | Katzakian, Jr. et al. |
| 4,017,429 A | 4/1977 | Steele et al. |
| 4,224,181 A | 9/1980 | Langer, Jr. |
| 4,603,184 A | 7/1986 | Sato et al. |
| 4,668,808 A | 5/1987 | Smith |
| 4,668,838 A | 5/1987 | Briggs |
| 4,716,206 A | 12/1987 | Fujita et al. |
| 4,721,762 A | 1/1988 | Commereuc et al. |
| 4,806,513 A | 2/1989 | McDaniel et al. |
| 4,814,308 A | 3/1989 | Konrad et al. |
| 5,198,563 A | 3/1993 | Reagen et al. |
| 5,288,823 A | 2/1994 | Reagan et al. |
| 5,331,070 A | 7/1994 | Pettijohn et al. |
| 5,331,104 A | 7/1994 | Reagen et al. |
| 5,340,785 A | 8/1994 | Reagen et al. |
| 5,360,879 A | 11/1994 | Reagen et al. |
| 5,376,612 A | 12/1994 | Reagen et al. |
| 5,382,738 A | 1/1995 | Reagen et al. |
| 5,393,719 A | 2/1995 | Pettijohn et al. |
| 5,399,539 A | 3/1995 | Reagen et al. |
| 5,438,027 A | 8/1995 | Reagen et al. |
| 5,451,645 A | 9/1995 | Reagen et al. |
| 5,470,926 A | 11/1995 | Reagen et al. |
| 5,523,507 A | 6/1996 | Reagen et al. |
| 5,543,375 A | 8/1996 | Lashier et al. |
| 5,563,312 A | 10/1996 | Knudsen et al. |
| 5,689,028 A | 11/1997 | Lashier et al. |
| 5,763,723 A | 6/1998 | Reagen et al. |
| 5,786,431 A | 7/1998 | Reagen et al. |
| 5,814,575 A | 9/1998 | Reagen et al. |
| 5,856,257 A | 1/1999 | Freeman et al. |
| 5,856,612 A | 1/1999 | Araki et al. |
| 5,859,303 A | 1/1999 | Lashier |
| 5,910,619 A | 6/1999 | Urata et al. |
| 5,919,996 A | 7/1999 | Freeman et al. |
| 5,986,153 A | 11/1999 | Kallenbach |
| 6,043,401 A | 3/2000 | Bagheri et al. |
| 6,133,495 A | 10/2000 | Urata et al. |
| 6,191,076 B1 | 2/2001 | Gee |
| 6,380,451 B1 | 4/2002 | Kreischer et al. |
| 6,455,648 B1 | 9/2002 | Freeman et al. |
| 6,521,806 B1 | 2/2003 | Tamura et al. |
| 7,045,632 B2 | 5/2006 | Small |
| 7,129,304 B1 | 10/2006 | Small et al. |
| 7,157,612 B2 | 1/2007 | Ewert et al. |
| 7,259,284 B2 | 8/2007 | Hope et al. |
| 7,268,096 B2 | 9/2007 | Small et al. |
| 7,271,121 B2 | 9/2007 | Small et al. |
| 7,297,832 B2 * | 11/2007 | Blann et al. .................. 585/527 |
| 7,309,805 B2 | 12/2007 | Hope et al. |
| 7,351,780 B2 | 4/2008 | Hope et al. |
| 7,378,537 B2 | 5/2008 | Small et al. |
| 7,384,886 B2 | 6/2008 | Knudsen et al. |
| 7,396,970 B1 | 7/2008 | Battiste |
| 7,425,661 B2 | 9/2008 | McConville et al. |
| 7,456,284 B2 | 11/2008 | Small |
| 7,476,775 B2 | 1/2009 | Kreischer |
| 2002/0182124 A1 | 12/2002 | Woodard et al. |
| 2004/0236163 A1 | 11/2004 | Ewert et al. |
| 2005/0187391 A1 | 8/2005 | Knudsen et al. |
| 2005/0197521 A1 | 9/2005 | Kreischer |
| 2005/0222350 A1 | 10/2005 | Small et al. |
| 2005/0255987 A1 | 11/2005 | McDaniel et al. |
| 2006/0247483 A1 | 11/2006 | McConville et al. |
| 2007/0185361 A1 | 8/2007 | Buchanan et al. |
| 2007/0185364 A1 | 8/2007 | Buchanan et al. |
| 2008/0051545 A1 | 2/2008 | McDaniel et al. |
| 2008/0058534 A1 | 3/2008 | Knudsen et al. |
| 2008/0177122 A1 | 7/2008 | Knudsen et al. |
| 2008/0293899 A1 | 11/2008 | McConville et al. |
| 2010/0030000 A1 | 2/2010 | Emoto et al. |
| 2010/0113852 A1 | 5/2010 | Sydora |
| 2010/0137669 A1 * | 6/2010 | Han et al. .................. 585/514 |

FOREIGN PATENT DOCUMENTS

| | | |
|---|---|---|
| EP | 0194596 A2 | 9/1986 |
| EP | 0207220 A2 | 1/1987 |
| EP | 0416304 A2 | 3/1991 |
| EP | 0608447 A1 | 8/1994 |
| EP | 0780353 A1 | 6/1997 |
| EP | 0608447 B1 | 10/2001 |
| FR | 2253029 | 6/1975 |
| WO | WO 97/11082 | 3/1997 |
| WO | WO 2006/109194 A2 | 10/2006 |
| WO | WO/2008/088178 * | 7/2008 |

OTHER PUBLICATIONS

Briggs, J., Chem. Commun., Selective Trimerization of Ethylene to Hex-1-ene, J. Chem. Soc., 1989, pp. 674-675.

Hart, Robert et al., "Synthesis and Structures of Metal Carboxylate Liquids," Shepherd Chemical Company, Mar. 23, 2009, National Meeting of the American Chemical Society.

Mehrotra, R.C. et al., "Metal Carboxylates," Jaipur 302004, 1983, Academic Press, pp. 22-27.

Mehrotra, R.C. et al., "Metal Carboxylates," Jaipur 302004, 1983, Academic Press, pp. 233-317.

Tille, D., Z. Anorg. Alleg. Chem., Organometal Compounds of Nitrogen Systems, 1971, 384, pp. 136-146.

Tille, D., Zeitschrift fur Naturforschung, Pyrrolylchromium Compounds, 1966, 21b, p. 1239.

International Search Report and Written Opinion for PCT/US2009/062700, Jan. 28, 2010.

U.S. Appl. No. 61/110,396, filed Oct. 31, 2008, entitled "System and Method for Diluting Metal Precursors for Oligomerization Catalyst Systems".

U.S. Appl. No. 61/110,407, filed Oct. 31, 2008, entitled "System and Method for Deactivating and Quenching an Oligomerization Catalyst".

U.S. Appl. No. 61/110,476, filed Oct. 31, 2008, entitled "Oligomerization Catalyst System and Process for Oligomerizing Olefins".

International Preliminary Report on Patentability for PCT/US2009/062700 mailed May 12, 2011, The International Bureau of WIPO, 7 pages.

U.S. Official Action dated Jun. 20, 2012 in U.S. Appl. No. 12/609,272, 17 pages.

* cited by examiner

OLIGOMERIZATION CATALYST SYSTEM AND PROCESS FOR OLIGOMERIZING OLEFINS

CROSS REFERENCE TO RELATED APPLICATIONS

This application is a Continuation-In-Part application to U.S. patent application Ser. No. 12/609,272 filed Oct. 30, 2009 which in turn claims priority to and the benefit of U.S. Provisional Patent Application No. 61/110,396 filed Oct. 31, 2008, U.S. Provisional Patent Application No. 61/110,407, filed Oct. 31, 2008, and U.S. Provisional Patent Application No. 61/110,476, filed Oct. 31, 2008. Each of these provisional patent applications is hereby incorporated by reference in its entirety.

TECHNICAL FIELD OF THE INVENTION

This disclosure relates to an oligomerization catalyst system, methods for preparing the oligomerization catalyst system, and methods for using the oligomerization catalyst system for preparing an oligomerization product.

BACKGROUND

The chromium-catalyzed synthesis of 1-hexene from ethylene constitutes a commercially significant process for the selective preparation of this alpha olefin, which in turn is useful for preparing a range of polyolefins when employed as a comonomer with ethylene. A widely reported chromium catalyst system for the selective production of 1-hexene comprises chromium(III) carboxylates (e.g. tris(2-ethylhexanoate) chromium(III) ($Cr(EH)_3$)), a pyrrole compound, and a metal alkyl.

Many oligomerization catalyst systems for the selective production of 1-hexene contain a chromium compound, a pyrrole compound, at least one metal alkyl, optionally a solvent, and optionally additional components, which can be combined in various ways and in various ratios to afford the catalyst system. Some catalyst system preparative methods appear to rely on the presence of particular solvent to stabilize the catalyst system. Typically, any method of preparing, activating, and using a catalyst system may present challenges with respect to its particular preparation, activation, and stability, as well as to the activity and selectivity provided by the catalyst system.

Therefore, it would be useful to discover and develop new oligomerization catalyst systems, new methods for preparing the oligomerization catalyst systems, and new methods for using the oligomerization catalyst systems for preparing an oligomerization product that might provide greater efficiency and cost effectiveness. New oligomerization catalyst systems and methods for preparing the oligomerization catalyst systems that might afford greater activity, increased efficiency, lower costs, increased selectivity to $C_6$ products (or to 1-hexene), and/or increased 1-hexene in the $C_6$ product fraction would be desirable.

SUMMARY OF THE INVENTION

Among other things, this disclosure provides for olefin oligomerization catalyst systems, methods for preparing the olefin oligomerization catalyst systems, and methods for using the olefin oligomerization catalyst system for preparing an oligomerization product. In one aspect, the oligomerization catalyst systems described here and prepared according to the various disclosed embodiments may allow for achieving good catalyst activity and selectivity.

In one aspect, this disclosure provides for a catalyst system comprising: a) a transition metal compound; b) a pyrrole compound having i) a hydrogen atom located on at least one pyrrole ring carbon atom adjacent to the nitrogen atom of the pyrrole ring, and ii) a bulky $C_3$ to $C_{18}$ organyl group or a bulky $C_3$ to $C_{60}$ silyl group located on a pyrrole ring carbon atom adjacent to any pyrrole ring carbon atom bearing the hydrogen atom adjacent to the nitrogen atom of the pyrrole ring; and c) a metal alkyl. In an embodiment, the bulky substituent located on pyrrole ring carbon atom adjacent to any pyrrole ring carbon atom bearing the hydrogen atom adjacent to the nitrogen atom of the pyrrole ring may have a structure such that i) the carbon atom of the bulky $C_3$ to $C_{18}$ organyl group attached to the pyrrole ring carbon atom is attached to three or four carbon atoms, ii) the carbon atom of the bulky $C_3$ to $C_{18}$ organyl group adjacent to the carbon atom attached to pyrrole ring carbon atom is attached to three or four carbon atoms, or iii) the silicon atom of the bulky $C_3$ to $C_{60}$ silyl group attached to the pyrrole ring carbon atom is attached to four carbon atoms.

In another aspect, the present disclosure provides for catalyst systems comprising a pyrrole compound having Formula P2, P3, or P4:

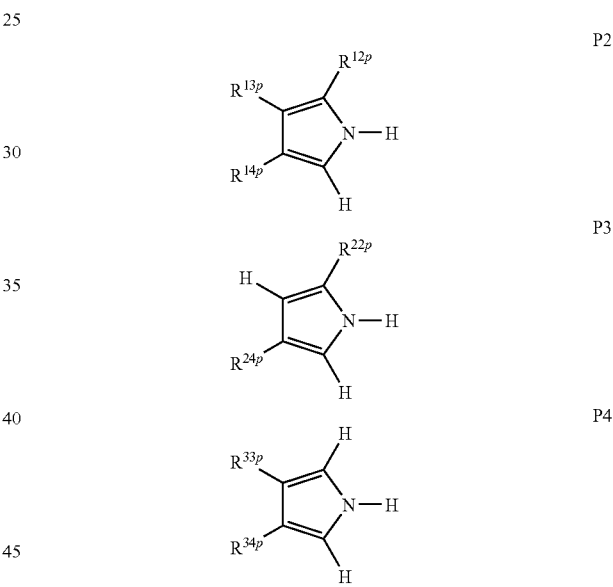

where i) $R^{12p}$ and $R^{13p}$ of Formula P2 and $R^{22p}$ of Formula P3 independently are a $C_1$ to $C_{15}$ hydrocarbyl group; and ii) $R^{14p}$ in Formula P2, $R^{24p}$ in Formula P3, and $R^{33p}$ and $R^{34p}$ in Formula P4 independently are a bulky $C_3$ to $C_{15}$ hydrocarbyl group or a bulky $C_3$ to $C_{45}$ silyl group. In an embodiment, the $R^{14p}$ group in Formula P2, $R^{24p}$ group in Formula P3, and $R^{33p}$ and $R^{34p}$ group in Formula P4 are attached such that i) the carbon atom attached to the pyrrole ring is attached to three or four carbon atoms, ii) the carbon atom adjacent to the carbon atom attached to pyrrole ring is attached to three or four carbon atoms, or iii) the $C_3$ to $C_{45}$ silyl group has Formula Si1:

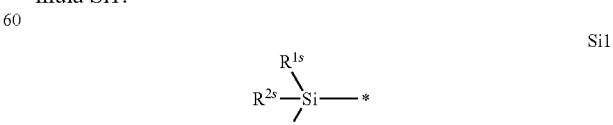

wherein $R^{1s}$, $R^{2s}$, and $R^{3s}$ independently are a $C_1$ to $C_{15}$ hydrocarbyl group.

In an aspect, the present disclosure provides for an oligomerization process comprising: A) contacting a feedstock olefin with a catalyst system comprising i) a transition metal compound; ii) a pyrrole compound having (a) a hydrogen atom located on at least one pyrrole ring carbon atom adjacent to the nitrogen atom of the pyrrole ring, and (b) a bulky $C_3$ to $C_{18}$ organyl group or a bulky $C_3$ to $C_{60}$ silyl group located on a pyrrole ring carbon atom adjacent to any pyrrole ring carbon atom bearing the hydrogen atom adjacent to the nitrogen atom of the pyrrole ring; and iii) a metal alkyl and B) oligomerizing the olefin under oligomerization condition to form an oligomerization product. In an embodiment, a bulky substituent located on pyrrole ring carbon atom adjacent to any pyrrole ring carbon atom bearing the hydrogen atom adjacent to the nitrogen atom of the pyrrole ring may have a structure such that i) the carbon atom of the bulky $C_3$ to $C_{18}$ organyl group attached to the pyrrole ring carbon atom is attached to three or four carbon atoms, ii) the carbon atom of the bulky $C_3$ to $C_{18}$ organyl group adjacent to the carbon atom attached to pyrrole ring carbon atom is attached to three or four carbon atoms, or iii) the silicon atom of the bulky $C_3$ to $C_{60}$ silyl group attached to the pyrrole ring carbon atom is attached to four carbon atoms.

In another aspect, the present invention provides for an trimerization process comprising: A) contacting a feedstock olefin comprising ethylene and a catalyst system comprising i) a transition metal compound comprising a chromium(II) or chromium(III) carboxylate wherein each carboxylate is a $C_4$ to $C_{19}$ carboxylate, ii) a pyrrole compound having Formula P2, P3, or P4:

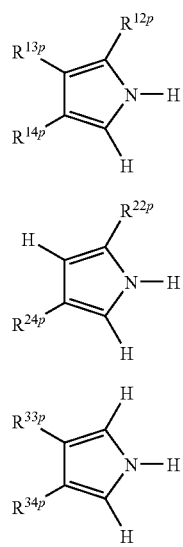

where (a) $R^{12p}$ and $R^{13p}$ of Formula P2 and $R^{22p}$ of Formula P3 independently are a $C_1$ to $C_{15}$ hydrocarbyl group and (b) $R^{14p}$ in Formula P2, $R^{24p}$ in Formula P3, and $R^{33p}$ and $R^{34p}$ in Formula P4 independently are a bulky $C_3$ to $C_{15}$ hydrocarbyl group or a bulky $C_3$ to $C_{45}$ silyl group, and iii) an metal alkyl comprising a mixture of triethylaluminum and diethylaluminum chloride; and B) trimerizing the feedstock olefin under trimerization conditions to form a trimerization product comprising 1-hexene. In an embodiment, the $R^{14p}$ group in Formula P2, $R^{24p}$ group in Formula P3, and $R^{33p}$ and $R^{34p}$ group in Formula P4 are attached such that i) the carbon atom attached to the pyrrole ring is attached to three or four carbon atoms, ii) the carbon atom adjacent to the carbon atom attached to pyrrole ring is attached to three or four carbon atoms, or iii) the $C_3$ to $C_{45}$ silyl group has Formula Si1:

wherein $R^{1s}$, $R^{2s}$, and $R^{3s}$ independently are a $C_1$ to $C_{15}$ hydrocarbyl group. In other embodiments, the trimerization process may have a higher productivity (g $C_6$/g transition metal—e.g. Cr) than the process using 2,4-dimethylpyrrole as the pyrrole compound, provide a higher selectivity to $C_6$ products than the process using 2,4-dimethylpyrrole as the pyrrole compound, and/or provide a higher purity 1-hexene product than the process using 2,4-dimethylpyrrole as the pyrrole compound.

In yet another aspect, this disclosure provides for a process for preparing a catalyst system, comprising contacting, a) a transition metal compound; b) a pyrrole compound having i) a hydrogen atom located on at least one pyrrole ring carbon atom adjacent to the nitrogen atom of the pyrrole ring, and ii) a bulky $C_3$ to $C_{18}$ organyl group or a bulky $C_3$ to $C_{60}$ silyl group located on a pyrrole ring carbon atom adjacent to any pyrrole ring carbon atom bearing the hydrogen atom adjacent to the nitrogen atom of the pyrrole ring; and c) a metal alkyl.

In a further aspect, this disclosure provides for a process for preparing a catalyst system, comprising contacting, a) a transition metal compound comprising a chromium(II) or chromium(III) carboxylate wherein each carboxylate is a $C_4$ to $C_{19}$ carboxylate; b) a pyrrole compound having Formula P2, P3, or P4:

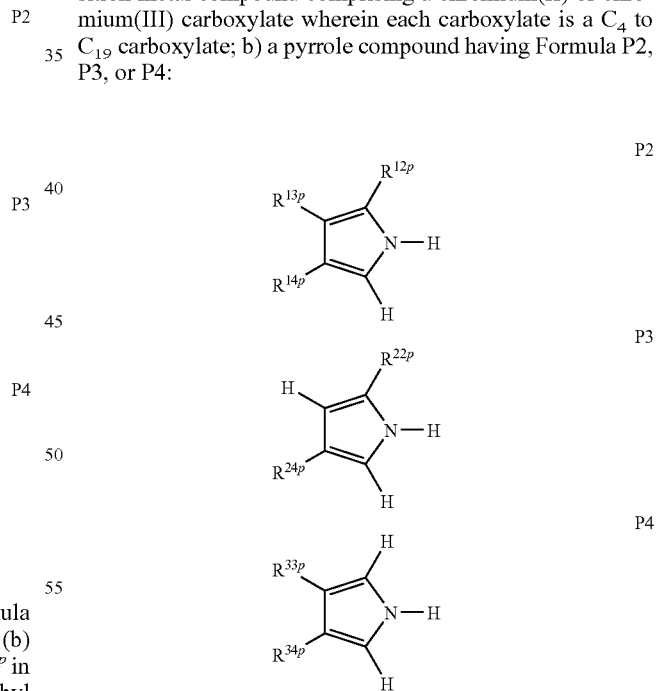

where i) $R^{12p}$ and $R^{13p}$ of Formula P2 and $R^{22p}$ of Formula P3 independently are a $C_1$ to $C_{15}$ hydrocarbyl group and ii) $R^{14p}$ in Formula P2, $R^{24p}$ in Formula P3, and $R^{33p}$ and $R^{34p}$ in Formula P4 independently are a bulky $C_3$ to $C_{15}$ hydrocarbyl group or a bulky $C_3$ to $C_{45}$ silyl group; and c) a metal alkyl comprising a mixture of triethylaluminum and diethylaluminum chloride,

DETAILED DESCRIPTION OF THE INVENTION

General Description

Figure 1:
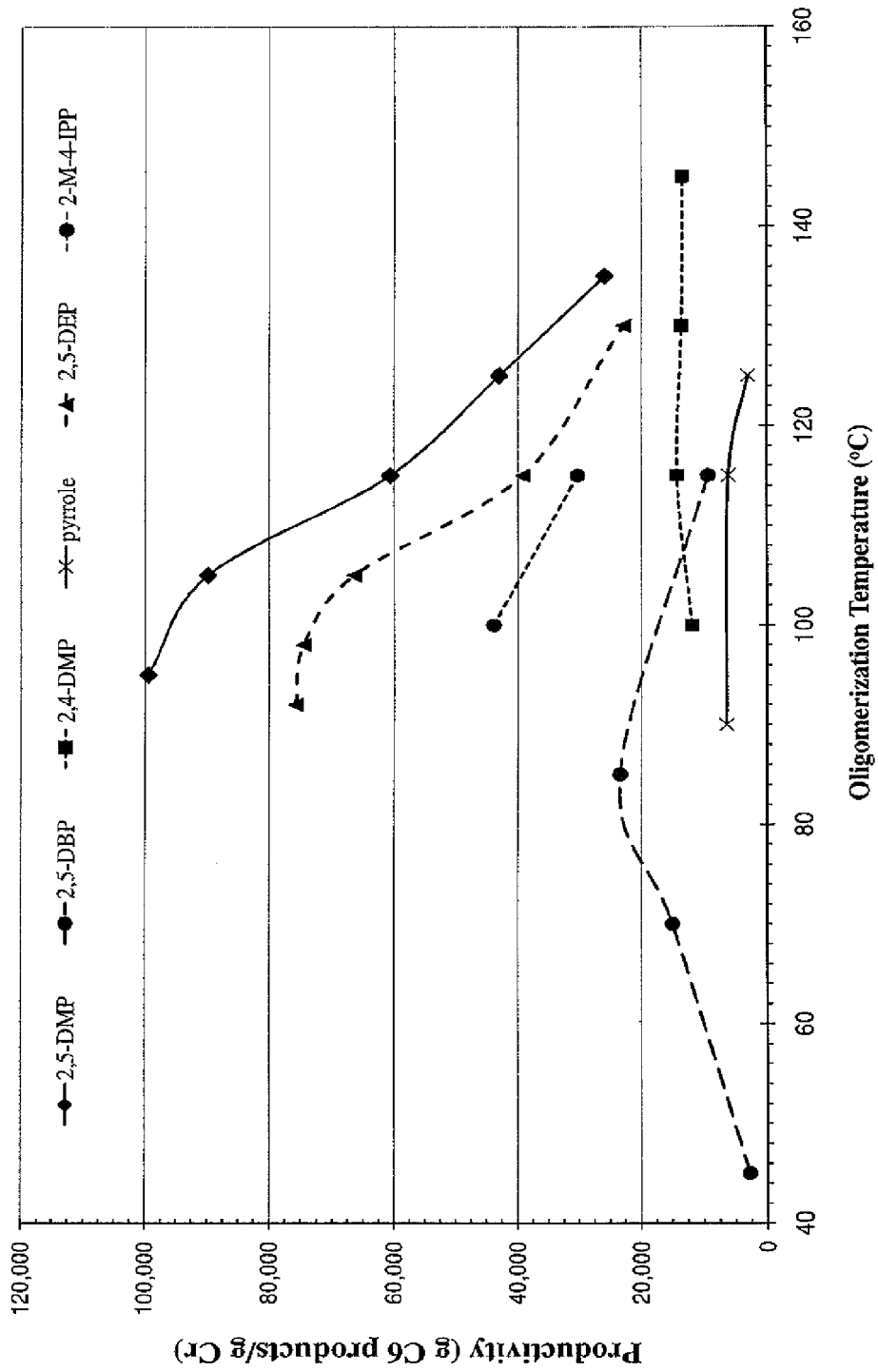
FIG. 1 is a plot of the $C_6$ catalyst productivity as a function of the oligomerization temperature for chromium-based catalyst systems containing certain pyrrole compounds.

According to various aspects and embodiments of this disclosure, there is provided olefin oligomerization catalyst systems, methods for their preparation, and methods for their use for preparing an olefin oligomerization product. In one aspect, the oligomerization catalyst systems described here and prepared according to the various disclosed embodiments can allow for achieving good catalyst system activity, catalyst system productivity, product selectivity, and/or product purity by selection of the pyrrole compound used in the catalyst system.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Regarding claim transitional terms or phrases, the transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to feature class to which is utilized and it is possible to have different transitional terms or phrases utilized with different features within a claim. For example a method can comprises several recited steps (and other non-recited steps) but utilize a catalyst system preparation consisting of specific steps but utilize a catalyst system comprising recited components and other non-recited components.

While compositions and methods are described in terms of "comprising" various components or steps, the compositions and methods can also "consist essentially of" or "consist of" the various components or steps.

The term "consists essentially of," or variations thereof, whenever used in this specification and claims in connection with a commercial product (e.g. a feedstock olefin such as ethylene) refers to a commercially available product. The commercially available product can contain impurities which are not the named product which are not removed during the commercial product's product process. One of ordinary skill in the art will recognize that the identity and quantity of the specific impurities present in the commercial product will depend upon the source of, and/or the manufacturing process used to produce the commercial product. Consequently, the term "consists essentially of" and its variants when used in conjunction with a commercial is not intended to limit the amount/quantity of the non-named product impurities any more stringently than the amounts/quantities present in a particular commercial product.

The terms "a," "an," and "the" are intended, unless specifically indicated otherwise, to include plural alternatives, e.g., at least one. For instance, the disclosure of "a chromium carboxylate" is meant to encompass chromium carboxylate, or mixtures or combinations of more than one chromium carboxylate unless otherwise specified.

In one aspect, a chemical "group" can be defined or described according to how that group is formally derived from a reference or "parent" compound, for example, by the number of hydrogen atoms that are formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials having three or more hydrogens atoms, as needed for the situation, removed from an alkane. Throughout, the disclosure that a substituent, ligand, or other chemical moiety may constitute a particular "group" implies that the well-known rules of chemical structure and bonding are followed when that group is employed as described. By way of example, if a subject compound is disclosed in which substituent X can be an "alkyl group," an "alkylene group," or an "alkane group," the normal rules of valence and bonding are followed. When describing a group as being "derived by," "derived from," "formed by," or "formed from," such terms are used in a formal sense and are not intended to reflect any specific synthetic methods or procedure, unless specified otherwise or the context requires otherwise.

Also, unless otherwise specified, any carbon-containing group for which the number of carbon atoms is not specified can have, according to proper chemical practice, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values. For example, unless otherwise specified, any carbon-containing group can have from 1 to 30 carbon atoms, from 1 to 25 carbon atoms, from 1 to 20 carbon atoms, from 1 to 15 carbon atoms, from 1 to 10 carbon atoms, or from 1 to 5 carbon atoms, and the like. Moreover, other identifiers or qualifying terms may be utilized to indicate the presence of, or absence of, a particular substituent, a particular regiochemistry, and/or stereochemistry, or the presence of absence of a branched underlying structure or backbone. Any specific carbon-containing group is limited according to the chemical and structural requirements for that specific group, as understood by one of ordinary skill. For example, unless otherwise specified, an aryl group can have from 6 to 30 carbon atoms, from 6 to 25 carbon atoms, from 6 to 20 carbon atoms, from 6 to 15 carbon atoms, or from 6 to 10 carbon atoms, and the like. Thus, according to proper chemical practice and unless otherwise specified, an aryl group can have 6, 7, 8, 9, 10, 11, 12, 13, 14, 15, 16, 17, 18, 19, 20, 21, 22, 23, 24, 25, 26, 27, 28, 29, or 30 carbon atoms, or any range or combination of ranges between these values.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group may also be referred to herein as "unsubstituted" or by equivalent terms such as "non-substituted," which refers to the original group or compound. "Substituted" is intended to be non-limiting and include inorganic substituents or organic substituents as specified and as understood by one of ordinary skill in the art.

A "halide" has its usual meaning. Examples of halides include fluoride, chloride, bromide, and iodide.

The term "hydrocarbon" whenever used in this specification and claims refers to a compound containing only carbon and hydrogen. Other identifiers may be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon (that is, a group containing only carbon and hydrogen). Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as needed for the particular group) from a hydrocarbon. A "hydrocarbyl group," "hydrocarbylene group," and "hydrocarbon group" can be acyclic or cyclic groups, and/or may be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene groups, alkyl, alkylene, alkane group, cycloalkyl, cycloalkylene, cycloalkane groups, aralkyl, aralkylene, and aralkane groups, respectively, among other groups as members.

An aliphatic compound is a non-aromatic organic compound. An "aliphatic group" is a generalized group formed by removing one or more hydrogen atoms (as needed for the particular group) from the carbon atoms of an aliphatic compound. An aliphatic compound may be acyclic or cyclic, saturated or unsaturated, and/or linear or branched organic compound. Aliphatic compounds and aliphatic groups may contain organic functional group(s) and/or atom(s) other than carbon and hydrogen.

The term "alkane" whenever used in this specification and claims refers to a saturated hydrocarbon compound. Other identifiers may be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as needed for the particular group) from an alkane. An "alkyl group," "alkylene group," and "alkane group" may be linear or branched unless otherwise specified. Primary, secondary, and tertiary alkyl group are derived by removal of a hydrogen atom from a primary, secondary, tertiary carbon atom, respectively, of an alkane. The n-alkyl group derived by removal of a hydrogen atom from a terminal carbon atom of a linear alkane. The groups $RCH_2$ ($R \neq H$), $R_2CH(R \neq H)$, and $R_3C(R \neq H)$ are primary, secondary, and tertiary alkyl groups, respectively. The carbon atom by which indicated moiety is attached is a secondary, tertiary, and quaternary carbon atom, respectively.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound (either two hydrogen atoms from one carbon atom or one hydrogen atom from each of two different carbon atoms). An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group that can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, and phosphines, and so forth. In one aspect, the hydrogen atom(s) removed to form the "organyl group," "organylene group," or "organic group" may be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" may be attached to a carbon atom not belonging to, and remote from, a functional group, for example, —CH$_2$C(O)CH$_3$, —CH$_2$NR$_2$, and the like. An "organyl group," "organylene group," or "organic group" may be aliphatic or aromatic, cyclic or acyclic, and/or linear or branched. "Organyl groups," "organylene groups," and "organic groups" also encompass heteroatom-containing rings, heteroatom-containing ring systems, heteroaromatic rings, and heteroaromatic ring systems. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, among others, as members.

For the purposes of this application, the term or variations of the term "organyl group consisting of inert functional groups" refers to an organyl group wherein the organic functional groups and/or atoms other than carbon and hydrogen present in the functional group are restricted to those functional groups and/or atoms other than carbon and hydrogen which are non-reactive under the process conditions defined herein. Thus, the term or variation of the term "organyl groups consisting of inert functional groups" further defines the particular organyl groups that can be present. Additionally, the term "organyl group consisting of inert functional groups" can refer to the presence of one or more inert functional groups within the organyl group. The term or variation of the "organyl group consisting of inert functional group" definition includes the hydrocarbyl group, among others, as a member.

For purposes of this application, an "inert functional group" is a group which does not substantially interfere with any process described herein in which it takes part (e.g. interfere with the oligomerization process). Non-limiting examples of inert functional groups which may not substantially interfere with any process described herein can include halogens (fluoro, chloro, bromo, and iodo), organoxy groups (e.g. hydrocarboxy group or alkoxy group among others), sulfidyl groups, and/or hydrocarbyl groups.

A cycloalkane is a saturated cyclic hydrocarbon, with or without side chains (e.g. cyclobutane or methylcyclobutane). Unsaturated cyclic hydrocarbons having one endocyclic double or one triple bond are called cycloalkenes and cycloalkynes, respectively. Those having more than one such multiple bond are cycloalkadienes, cycloalkatrienes, and so forth.

A "cycloalkyl group" is a univalent group derived by removing a hydrogen atom from a ring carbon atom from a cycloalkane. For example, a 1-methylcyclopropyl group and a 2-methylcyclopropyl group are illustrated as follows.

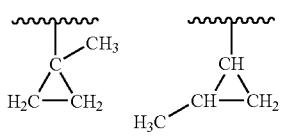

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as needed for the particular group and at least one of which is a ring carbon) from a cycloalkane.

The term "alkene" whenever used in this specification and claims refers to a compound that has at least one non-aromatic carbon-carbon double bond. The term "alkene" includes aliphatic or aromatic, cyclic or acyclic, and/or linear and branched alkenes unless expressly stated otherwise. The term "alkene," by itself, does not indicate the presence or absence of heteroatoms and/or the presence or absence of other carbon-carbon double bonds unless explicitly indicated. The terms "hydrocarbon alkene" or "alkene hydrocarbon" refer to alkenes containing only hydrogen and carbon. Other identifiers may be utilized to indicate the presence or absence of particular groups within an alkene. Alkenes may also be further identified by the position of the carbon-carbon double bond. Alkenes, having more than one such multiple bond are alkadienes, alkatrienes, and so forth. The alkene may be further identified by the position of the carbon-carbon double bond(s).

An "alkenyl group" is a univalent group derived from an alkene by removal of a hydrogen atom from any carbon atom of the alkene. Thus, "alkenyl group" includes groups in which the hydrogen atom is formally removed from an $sp^2$ hybridized (olefinic) carbon atom and groups in which the hydrogen atom is formally removed from any other carbon atom. For example and unless otherwise specified, propen-1-yl (—CH=CHCH$_3$), propen-2-yl [(CH$_3$)C=CH$_2$], and propen-3-yl (—CH$_2$CH=CH$_2$) groups are all encompassed with the term "alkenyl group." Similarly, an "alkenylene group" refers to a group formed by formally removing two hydrogen atoms from an alkene, either two hydrogen atoms from one carbon atom or one hydrogen atom from two different carbon atoms. An "alkene group" refers to a generalized group formed by removing one or more hydrogen atoms (as needed for the particular group) from an alkene. When the hydrogen atom is removed from a carbon atom participating in a carbon-carbon double bond, the regiochemistry of the carbon from which the hydrogen atom is removed, and regiochemistry of the carbon-carbon double bond may both be specified. The terms "alkenyl group," "alkenylene group," and "alkene group" by themselves do not indicate the presence or absence of heteroatoms and/or the presence or absence of other carbon-carbon double bonds unless explicitly indicated. The terms "hydrocarbon alkenyl group," "hydrocarbon alkenylene group," and "hydrocarbon alkene group" refer to alkene groups containing only hydrogen and carbon. Other identifiers may be utilized to indicate the presence or absence of particular groups within an alkene group. Alkenyl groups may also have more than one such multiple bond. The alkene group may also be further identified by the position of the carbon-carbon double bond(s).

The term "alkyne" is used in this specification and claims to refer to a compound that has at least one carbon-carbon triple bond. The term "alkyne" includes aliphatic or aromatic, cyclic or acyclic, and/or linear and branched alkynes unless expressly stated otherwise. The term "alkyne," by itself, does not indicate the presence or absence of heteroatoms and/or the presence or absence of other carbon-carbon triple bonds unless explicitly indicated. The terms "hydrocarbon alkyne" or "alkyne hydrocarbon" refer to alkyne compounds containing only hydrogen and carbon. Other identifiers may be utilized to indicate the presence or absence of particular groups within an alkyne. Alkynes, having more than one such multiple bond are alkadiynes, alkatriynes, and so forth. The alkyne group may also be further identified by the position of the carbon-carbon triple bond(s).

An "alkynyl group" is a univalent group derived from an alkyne by removal of a hydrogen atom from any carbon atom of the alkyne. Thus, "alkynyl group" includes groups in which the hydrogen atom is formally removed from an sp hybridized (acetylenic) carbon atom and groups in which the hydrogen atom is formally removed from any other carbon atom. For example and unless otherwise specified, 1-propyn-1-yl (—C≡CCH$_3$) and propyn-3-yl (HC≡CCH$_2$—) groups are all encompassed with the term "alkynyl group." Similarly, an "alkynylene group" refers to a group formed by formally removing two hydrogen atoms from an alkyne, either two hydrogen atoms from one carbon atom if possible or one hydrogen atom from two different carbon atoms. An "alkyne group" refers to a generalized group formed by removing one or more hydrogen atoms (as needed for the particular group) from an alkyne. The terms "alkynyl group," "alkynylene group," and "alkyne group" by themselves do not indicate the presence or absence of heteroatoms and/or the presence or absence of other carbon-carbon double bonds unless explicitly indicated. The terms "hydrocarbon alkynyl group," "hydrocarbon alkynylene group," and "hydrocarbon alkyne group" refer to olefin groups containing only hydrogen and carbon. Other identifiers may be utilized to indicate the presence or absence of particular groups within an alkyne group. Alkyne groups may have more than one such multiple bond. Alkyne groups may also be further identified by the position of the carbon-carbon triple bond(s).

The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise. In the case of branched alpha olefins, a branch may be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

An "aromatic group" refers to a generalized group formed by removing one or more hydrogen atoms (as needed for the particular group and at least one of which is an aromatic ring carbon atom) from an aromatic compound. Thus, an "aromatic group" as used herein refers to a group derived by removing one or more hydrogen atoms from an aromatic compound, that is, a compound containing a cyclically conjugated hydrocarbon that follows the Hückel (4n+2) rule and containing (4n+2) pi-electrons, where n is an integer from 1 to about 5. Aromatic compounds and hence "aromatic groups" may be monocyclic or polycyclic unless otherwise specified. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms by trivalent or divalent heteroatoms, in such a way as to maintain the continuous pi-electron system characteristic of aromatic systems and a number of out-of-plane pi-electrons corresponding to the Hückel rule (4n+2). While arenes and heteroarenes are mutually exclusive members of the group of aromatic compounds, a compound that has both an arene group and a heteroarene group that compound generally is considered a heteroarene compound. Aromatic compounds, arenes, and heteroarenes may be mono- or polycyclic unless otherwise specified. Examples of arenes include, but are not limited to, benzene, naphthalene, and toluene, among others. Examples of heteroarenes include, but are not limited to furan, pyridine, and methylpyridine, among others. As disclosed herein, the term "substituted" may be used to describe an aromatic group wherein any non-hydrogen moiety formally replaces a hydrogen in that group, and is intended to be non-limiting.

An "aryl group" refers to a generalized group formed by removing a hydrogen atom from an aromatic hydrocarbon ring carbon atom from an arene. One example of an "aryl group" is ortho-tolyl (o-tolyl), the structure of which is shown here.

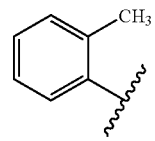 [SMILES: *c1ccccc1C]

Similarly, an "arylene group" refers to a group formed by removing two hydrogen atoms (at least one of which is from an aromatic hydrocarbon ring carbon) from an arene. An "arene group" refers to a generalized group formed by removing one or more hydrogen atoms (as needed for the particular group and at least one of which is an aromatic hydrocarbon ring carbon) from an arene. However, if a group contains separate and distinct arene and heteroarene rings or ring systems (e.g. the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g. the 2 carbon atom in the phenyl group of 6-phenylbenzofuran) and a heteroarene group if the removed hydrogen carbon came from a heteroaromatic ring or ring system carbon atom (e.g. the 2 or 7 carbon atom of the benzofuran group of 6-phenylbenzofuran).

An "aralkyl group" is an aryl-substituted alkyl group having a free valance at a non-aromatic carbon atom, for example, a benzyl group is an "aralkyl" group. Similarly, an "aralkylene group" is an aryl-substituted alkylene group having two free valances at a single non-aromatic carbon atom or a free valence at two non-aromatic carbon atoms while an "aralkane group" is a generalized is an aryl-substituted alkane group having one or more free valances at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having a two free valances at a single non-heteroaromatic ring or ring system carbon atom or a free valences at two non-heteroaromatic ring or ring system carbon atoms while a "heteroaralkane group" is a generalized aryl-substituted alkane group having one or more free valances at a non-heteroaromatic ring or ring system carbon atom(s).

If a compound or group contains more than one moiety it is formally a member of the group having the highest naming priority as stipulated by IUPAC. For example 4-phenyl-pyridine is a heteroaromatic compound and a 4-(phen-2-ylene)pyridin-2-yl group is a hetero-aromatic group because the highest naming groups is the pyridine group and the pyridin-2-yl group respectively.

A silane is a compound containing a silicone atom. A "silyl group" is a generalized group formed by removing a hydrogen atom from the silicon atom of a silane.

An "organoaluminum compound," is used to describe any compound that contains an aluminum-carbon bond. Thus, organoaluminum compounds include hydrocarbyl aluminum compounds such as trialkyl-, dialkyl-, or monoalkylaluminum compounds; hydrocarbyl alumoxane compounds, and aluminate compounds which contain an aluminum-organyl bond such as tetrakis(p-tolyl)aluminate salts.

The term "reactor effluent," and it derivatives (e.g. oligomerization reactor effluent) generally refers to all the material which exits the reactor. The term "reactor effluent," and its derivatives, may also be prefaced with other descriptors that limit the portion of the reactor effluent being referenced. For example, while the term "reactor effluent" would refer to all material exiting the reactor (e.g. Product and solvent or diluent, among others), the term "olefin reactor effluent" refers to the effluent of the reactor which contains an olefin (i.e. carbon-carbon) double bond.

The term "oligomerization," and its derivatives, refers to processes which produce a mixture of products containing at least 70 weight percent products containing from 2 to 30 monomer units. Similarly, an "oligomer" is a product that contains from 2 to 30 monomer units while an "oligomerization product" includes all products made by the "oligomerization" process including the "oligomers" and products produced by the process which are not "oligomers" (e.g. product which contain more than 30 monomer units. It should be noted that the monomer units in the "oligomer" or "oligomerization product" do not have to be the same. For example, an "oligomer" or "oligomerization product" of an "oligomerization" process using ethylene and propylene as monomers may contain both ethylene and/or propylene units.

The term "trimerization," and it derivatives, refers to a process which produces a product containing at least 70 weight percent products containing three and only three monomer units. A "trimer" is a product which contains three and only three monomer units while a "trimerization product" includes all products made by the trimerization process including trimer and products which are not trimer (e.g. dimers or tetramers). Generally, an olefin trimerization reduces number of olefinic bonds, i.e., carbon-carbon double bonds, by two when considering the number of olefin bonds in the monomer units and the number of olefin bonds in the trimer. It should be noted that the monomer units in the "trimer" or "trimerization product" do not have be the same. For example, a "trimer" of a "trimerization" process using ethylene and butene as monomers may contain ethylene and/or butene monomer units. That is to say the "trimer" may include $C_6$, $C_8$, $C_{10}$, and $C_{12}$ products. In another example, a "trimer" of a "trimerization" process using ethylene as the monomer may contain ethylene monomer units. It should also be noted that a single molecule may contain two monomer units. For example, dienes such as 1,3-butadiene and 1,4-pentadiene have two monomer units within one molecule.

Oligomerization Catalyst System

The oligomerization catalyst system minimally comprises a transition metal compound, a pyrrole compound, and a metal alkyl. In another aspect, the oligomerization catalyst system may further comprise a halogen containing compound. The transition metal compound, pyrrole compound, metal alkyl, and optional halogen containing compound are independent elements of the oligomerization catalyst system. These elements of the oligomerization catalyst system are independently described herein and the catalyst system may be further described utilizing any combination of the transition metal described herein, the pyrrole compound described herein, metal alkyl described herein, and optional halogen containing compound described herein.

Transition Metal Compound

Generally, the transition metal compound for the oligomerization catalyst system can comprise, consist essentially of, or consist of, a group 5, 6, 7, 8, 9, 10, or 11 transition metal. In some embodiments, the transition metal compound comprises, consists essentially of, or consists of, chromium, nickel, cobalt, iron, molybdenum, or copper. In other embodiments, the transition metal compound comprises, consists essentially of, or consists of, chromium.

In some aspects, the transition metal compound for the oligomerization catalyst system may be an inorganic transition metal compound. In other aspects, the transition metal compound may contain ligands formally derived from an organic compound or moiety (e.g. a carboxylate, alkoxide, or beta-dionate, among others). In an embodiment, suitable inorganic transition metal compounds include, but are not limited to, a transition metal halide, a transition metal sulfate, a transition metal sulfite, a transition metal bisulfate, a transition metal oxide, a transition metal nitrate, a transition metal nitrite, a transition metal hydroxide, a transition metal chlorate, or any combinations thereof; alternatively, transition metal halide, a transition metal sulfate, a transition metal oxide, or a transition metal nitrate. In an embodiment, the transition metal halide may be a transition metal chloride, a transition metal bromide, or a transition metal iodide. In an embodiment, the transition metal compound may be a transition metal alkoxide, a transition metal aryloxide, a transition metal carboxylate, a transition metal beta-dionate (such as an acetylacetonate), or a transition metal amide compound; alternatively, a transition metal alkoxide or transition metal aryloxide; alternatively, a transition metal carboxylate, a transition metal beta-dionate; or alternatively, a transition metal amide. Further, in another aspect, suitable transition metal compounds can contain combinations of these recited ligands. In some embodiments, the transition metal compound comprises, consists essentially of, or consists of, a transition metal carboxylate.

Alternatively, and in any aspect and embodiment, suitable transition metal compounds may comprise, consist essentially of, or consist of, a transition metal halide; alternatively, a transition metal sulfate; alternatively, a transition metal sulfite; alternatively, a transition metal bisulfate; alternatively, a transition metal oxide; alternatively, a transition metal nitrate; alternatively, a transition metal nitrite; alternatively, a transition metal hydroxide; alternatively, a transition metal alkoxide; alternatively, a transition metal aryloxide; alternatively, a transition metal carboxylate; alternatively, a transition metal beta-dionate; alternatively, a transition metal chlorate; or alternatively, a transition metal amide. In an embodiment, the transition metal halide may be a transition metal chloride; alternatively, a transition metal bromide; or alternatively, a transition metal iodide.

According to a further aspect of this disclosure and in any embodiment, each hydrocarboxy group (alkoxy or aryloxy), carboxylate group, beta-dionate group, or amide group of the transition metal compound may be a $C_1$ to $C_{24}$, a $C_4$ to $C_{19}$, or a $C_5$ to $C_{12}$ hydrocarboxy group (alkoxy or aryloxy), carboxylate group, beta-dionate group, or amide group. In an embodiment, each carboxylate group of the transition metal compound may be a $C_2$ to $C_{24}$ carboxylate group; alternatively, a $C_4$ to $C_{19}$ carboxylate group; or alternatively, a $C_s$ to $C_{12}$ carboxylate group. In some embodiments, each alkoxy group of the transition metal compound may be a $C_1$ to $C_{24}$ alkoxy group; alternatively, a $C_4$ to $C_{19}$ alkoxy group; or alternatively, a $C_5$ to $C_{12}$ alkoxy group. In other embodiments, each aryloxy group of the transition metal compound may be a $C_6$ to $C_{24}$ alkoxy group; alternatively, a $C_6$ to $C_{19}$ alkoxy group; or alternatively, a $C_6$ to $C_{12}$ alkoxy group. In yet other embodiments, each beta-dionate group of the transition metal compound may be a $C_5$ to $C_{24}$ beta-dionate group; alternatively, a $C_5$ to $C_{19}$ beta-dionate group; or alternatively, a $C_5$ to $C_{12}$ beta-dionate group. In further embodiments, amide group of the transition metal compound may be a $C_1$ to $C_{24}$ amide group; alternatively, a $C_3$ to $C_{19}$ amide group; or alternatively, a $C_4$ to $C_{12}$ amide group. In some embodiments, the carboxylate of the transition metal carboxylate may be monocarboxylate.

According to a further aspect of this disclosure and in any embodiment, the transition metal of the transition metal compound can have an oxidation state of 0, +1 (or 1), +2 (or 2), +3 (or 3), +4 (or 4), +5 (or 5), or +6 (or 6), respectively. In another aspect and in other embodiments, the transition metal compound can have an oxidation state of +2 or +3; or alternatively, the transition metal compound can have an oxidation state of +3. Further to this aspect and in any embodiment, the transition metal compound can have an oxidation state of 0; alternatively, +1; alternatively, +2; alternatively, +3; alternatively, +4; alternatively, +5; or alternatively, +6.

In still a further aspect of this disclosure, the transition metal compound of the oligomerization catalyst system may comprise, consist essentially of, or consist of, a chromium compound. In this aspect, the chromium compound can have a chromium oxidation state of 0 to 6. In some embodiments, the chromium within the chromium compound may have an oxidation state of 2 or 3 (i.e., a chromium(II) or chromium (III) compound). In other embodiments, the chromium within the chromium compound can have an oxidation state of 2 (i.e. a chromium(II) compound); or alternatively, have an oxidation state of 3 (i.e. a chromium(III) compound). For example, chromium(II) compounds which may be used as the transition metal compound for the oligomerization catalyst system may comprise, consist essentially of, or consist of, chromium (II) nitrate, chromium(II) sulfate, chromium(II) fluoride, chromium(II) chloride, chromium(II) bromide, or chromium (II) iodide. Also by way of example, the chromium(III) compounds which may be used as the transition metal compound for the oligomerization catalyst system may comprise, consist essentially of, or consist of, chromium(III) nitrate, chromium(III) sulfate, chromium(III) fluoride, chromium(III) chloride, chromium(III) bromide, or chromium(III) iodide. Alternatively, the chromium compounds that can be used as the transition metal compound for the oligomerization catalyst system may comprise, consist essentially of, or consist of, chromium(II) nitrate; alternatively, chromium(II) sulfate; alternatively, chromium(II) fluoride; alternatively, chromium (II) chloride; alternatively, chromium(II) bromide; alternatively, chromium(II) iodide; alternatively, chromium(III) nitrate; alternatively, chromium(III) sulfate; alternatively, chromium(III) fluoride; alternatively, chromium(III) chloride; alternatively, chromium(III) bromide; or alternatively, chromium(III) iodide.

In yet an additional aspect of this disclosure and in any embodiment, the transition metal compound for the oligomerization catalyst system comprise, consist essentially of, or consist of, a chromium(II) alkoxide, a chromium(II) carboxylate, a chromium(II) beta-dionate, a chromium(III) alkoxide, a chromium(III) carboxylate, or a chromium(III) beta-dionate; alternatively, a chromium(II) alkoxide or a chromium (III) alkoxide; alternatively, a chromium(II) carboxylate or a chromium(III) carboxylate; alternatively, a chromium(II) beta-dionate or a chromium(III) beta-dionate; alternatively, a chromium(II) alkoxide; alternatively, a chromium(II) carboxylate; alternatively, a chromium(II) beta-dionate; alternatively, a chromium(III) alkoxide; alternatively, a chromium (III) carboxylate; or alternatively, a chromium(III) beta-dionate. In an embodiment, each carboxylate group of the chromium compound may be a $C_2$ to $C_{24}$ carboxylate group; alternatively, a $C_4$ to $C_{19}$ carboxylate group; or alternatively, a $C_5$ to $C_{12}$ carboxylate group. In some embodiments, each alkoxy group of the chromium compound may be a $C_1$ to $C_{24}$ alkoxy group; alternatively, a $C_4$ to $C_{19}$ alkoxy group; or alternatively, a $C_5$ to $C_{12}$ alkoxy group. In other embodiments, each aryloxy group of the chromium compound may be a $C_6$ to $C_{24}$ aryloxy group; alternatively, a $C_6$ to $C_{19}$ aryloxy group; or alternatively, a $C_6$ to $C_{12}$ aryloxy group. In yet other embodiments, each beta-dionate group of the chromium compound may be a $C_5$ to $C_{24}$ beta-dionate group; alternatively, a $C_5$ to $C_{19}$ beta-dionate group; or alternatively, a $C_5$ to $C_{12}$ beta-dionate group. In further embodiments, amide group of the chromium compound may be a $C_1$ to $C_{24}$ amide group; alternatively, a $C_3$ to $C_{19}$ amide group; or alternatively, a $C_4$ to $C_{12}$ amide group.

Chromium carboxylates are particularly useful transition metal compounds for the oligomerization catalyst system. Thus, in one aspect, the catalyst system and process according to this disclosure provides for the use of chromium carboxylate compositions, including but are not limited to, chromium carboxylate compositions in which the carboxylate is a $C_2$ to $C_{24}$ monocarboxylate; alternatively, a $C_4$ to $C_{19}$ monocarboxylate; or alternatively, a $C_s$ to $C_{12}$ monocarboxylate. Some widely employed chromium carboxylate composition catalysts are those of chromium(III), for example, chromium (III) compositions comprising 2-ethylhexanoate are effective catalyst system components for selective 1-hexene synthesis.

In one aspect, the carboxylate group of the chromium carboxylate may be a $C_2$ to $C_{24}$ monocarboxylate. In an embodiment, the carboxylate group of the chromium carboxylate may be an acetate, a propionate, a butyrate, a pentanoate, a hexanoate, a heptanoate, an octanoate, a nonanoate, a decanoate, an undecanoate, a dodecanoate, a tridecanoate, a tetradecanoate, a pentadecanoate, a hexadecanoate, a heptadecanoate, or an octadecanoate; or alternatively, a pentanoate, a hexanoate, a heptanoate, a octanoate, a nonanoate, a decanoate, a undecanoate, or a dodecanoate. In some embodiments, the carboxylate group of the chromium carboxylate may be acetate, propionate, n-butyrate, isobutyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, laurate (n-dodecanoate), or stearate (n-octadecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, acetate; alternatively, propionate; alternatively, n-butyrate; alternatively, isobutyrate; alternatively, valerate (n-pentanoate); alternatively, neo-pentanoate; alternatively, capronate (n-hexanoate); alternatively, n-heptanoate; alternatively, caprylate (n-octanoate); alternatively, 2-ethylhexanoate; alternatively, n-nonanoate; alternatively, caprate (n-decanoate); alternatively, n-undecanoate; alternatively, laurate (n-dodecanoate); or alternatively, stearate (n-octadecanoate).

In an aspect and in any embodiment, the transition metal compound for the oligomerization catalyst system may comprise, consist essentially of, or consist of, a chromium(II) carboxylate; or alternatively, a chromium(III) carboxylate. Exemplary chromium(II) carboxylates may include, but are not limited to, chromium(II) acetate, chromium(II) propionate, chromium(II) butyrate, chromium(II) isobutyrate, chromium(II) neopentanoate, chromium(II) oxalate, chromium(II) octanoate, chromium(II) (2-ethylhexanoate), chromium(II) laurate, or chromium(II) stearate; or alternatively, chromium(II) acetate, chromium(II) propionate, chromium(II) butyrate, chromium(II) isobutyrate, chromium(II) neopentanoate, chromium(II) octanoate, chromium(II) (2-ethylhexanoate), chromium(II) laurate, or chromium(II) stearate. In an aspect and in any embodiment, the transition metal compound utilized in the catalyst system may comprise, consist essentially of, or consist of, chromium(III) acetate, chromium(III) propionate, chromium(III) butyrate, chromium(III) isobutyrate, chromium(III) neopentanoate, chromium(III) oxalate, chromium(III) octanoate, chromium(III) 2-ethylhexanoate, chromium(III) 2,2,6,6-tetramethylheptanedionate, chromium(III) naphthenate, chromium(III) laurate, or chromium(III) stearate; or alternatively, chromium(III) acetate, chromium(III) propionate, chromium(III) butyrate, chromium(III) isobutyrate, chromium(III) neopentanoate, chromium(III) octanoate, chromium(III) 2-ethylhexanoate, chromium(III) 2,2,6,6-tetramethylheptanedionate, chromium(III) naphthenate, chromium(III) laurate, or chromium(III) stearate. In a further aspect and in any number of embodiments, the transition metal compound for the oligomerization catalyst system may comprise, consist essentially of, or consist of, chromium(II) acetate; alternatively, chromium(II) propionate; alternatively, chromium(II) butyrate; alternatively, chromium(II) isobutyrate; alternatively, chromium(II) neopentanoate; alternatively, chromium(II) oxalate; alternatively, chromium(II) octanoate; alternatively, chromium(II) (2-ethylhexanoate); alternatively, chromium(II) laurate; alternatively, chromium(II) stearate; alternatively, chromium(III) acetate; alternatively, chromium(III) propionate; alternatively, chromium(III) butyrate; alternatively, chromium(III) isobutyrate; alternatively, chromium(III) neopentanoate; alternatively, chromium(III) oxalate; alternatively, chromium(III) octanoate; alternatively, chromium(III) 2-ethylhexanoate; alternatively, chromium(III) 2,2,6,6-tetramethylheptane dionate; alternatively, chromium(III) naphthenate; alternatively, chromium(III) laurate; or alternatively, chromium(III) stearate. In some embodiments, the transition metal compound for the oligomerization catalyst system may comprise, consist essentially of, or consist of, chromium(II) 2-ethylhexanoate or chromium(III) 2-ethylhexanoate; or alternatively chromium(III) 2-ethylhexanoate.

Pyrrole Compound

In an aspect, the pyrrole compound (also called the "pyrrole") of the oligomerization catalyst system can comprise, consist essentially of, or consist of, any pyrrole compound that will react with a chromium source to form a transition metal pyrrolide complex (e.g. chromium pyrrolide complex). As used in this disclosure, the term "pyrrole compound" refers to pyrrole ($C_5H_5N$), derivatives of pyrrole (e.g. indole), substituted pyrroles, as well as metal pyrrolide complexes. A pyrrole compound is defined as a compound comprising a 5-membered, nitrogen-containing heterocycle, such as for example, pyrrole, derivatives of pyrrole, and mixtures thereof. Broadly, the pyrrole compound may be pyrrole or any heteroleptic or homoleptic metal complex or salt containing a pyrrolide radical or ligand.

Generally, the pyrrole compound may be a $C_4$ to $C_{20}$, or $C_4$ to $C_{10}$ pyrrole. Exemplary pyrrole compounds that may be used in the oligomerization catalyst system include, but are not limited to pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, pyrrole, 2,5-dimethylpyrrole, 3,4-dimethylpyrrole, 3,4-dichloropyrrole, 2,5-diethylpyrrole, 2-methyl-5-ethylpyrrole, 2-methyl-5-propylpyrrole, 2,3,4,5-tetrachloropyrrole, 2-acetylpyrrole, pyrazole, pyrrolidine, indole, and dipyrrolomethane, and mixtures thereof, among others. Pyrrolides that may be used as the nitrogen compound include diethylaluminum 2,5-dimethylpyrrolide; ethylaluminum di(2,5-dimethylpyrrolide); and aluminum tri(2,5-dimethylpyrrolide); among others.

In an aspect, the pyrrole compound may have Formula P1 or Formula I1. In an embodiment, the pyrrole compound may have Formula P1; or alternatively Formula I1.

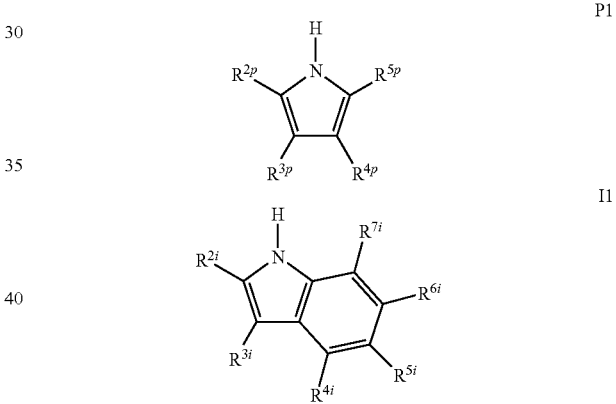

In an aspect, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 may independently be a hydrogen, a $C_1$ to $C_{18}$ organyl group, or a $C_3$ to $C_{60}$ silyl group; alternatively, hydrogen, a $C_1$ to $C_{15}$ organyl group, or a $C_3$ to $C_{45}$ silyl group; alternatively, hydrogen, a $C_1$ to $C_{10}$ organyl group, or a $C_3$ to $C_{30}$ silyl group; alternatively, hydrogen, a $C_1$ to $C_5$ organyl group, or a $C_3$ to $C_{15}$ silyl group; alternatively, hydrogen or a $C_1$ to $C_{18}$ organyl group; alternatively, hydrogen or a $C_1$ to $C_{15}$ organyl group; alternatively, hydrogen or a $C_1$ to $C_{10}$ organyl group; or alternatively, hydrogen or a $C_1$ to $C_5$ organyl group. In an embodiment, $R^{2p}$, $R^{3p}$, $R^{4p}$, and $R^{5p}$ of Formula P1 and $R^{2i}$, $R^{3i}$, $R^{4i}$, $R^{5i}$, $R^{6i}$, and $R^{7i}$ of Formula I1 may independently be a hydrogen, a $C_1$ to $C_{18}$ hydrocarbyl group, or a $C_3$ to $C_{60}$ silyl group; alternatively, hydrogen, a $C_1$ to $C_{15}$ hydrocarbyl group, or a $C_3$ to $C_{45}$ silyl group; alternatively, hydrogen, a $C_1$ to $C_{10}$ hydrocarbyl group, or a $C_3$ to $C_{35}$ silyl group; alternatively, hydrogen, a $C_1$ to $C_5$ hydrocarbyl group, or a $C_3$ to $C_{15}$ silyl group; alternatively, hydrogen or a $C_1$ to $C_{18}$ hydrocarbyl group; alternatively, hydrogen or a $C_1$ to $C_{15}$ hydrocarbyl group; alternatively, hydrogen or a $C_1$ to $C_{10}$ hydrocarbyl group; or alternatively, hydrogen or a $C_1$ to $C_5$ hydrocarbyl group.

In an embodiment wherein the pyrrole compound has Formula P1, $R^{3p}$ and $R^{4p}$ may be hydrogen and $R^{2p}$ and $R^{5p}$ may be any non-hydrogen pyrrole substituent described herein; alternatively, $R^{2p}$ and $R^{5p}$ may be hydrogen and $R^{3p}$ and $R^{4p}$ may be any non-hydrogen pyrrole substituent described herein; or alternatively, $R^{2p}$ and $R^{4p}$ may be hydrogen and $R^{3p}$ and $R^{5p}$ may be any non-hydrogen pyrrole substituent described herein. In some embodiments, $R^{2p}$, $R^{3p}$, and $R^{5p}$ may be hydrogen and $R^{4p}$ may be any non-hydrogen pyrrole substituent described herein; alternatively, $R^{2p}$, $R^{3p}$, and $R^{4p}$ may be hydrogen and $R^{5p}$ may be any non-hydrogen pyrrole substituent described herein; or alternatively, $R^{2p}$ may be hydrogen and $R^{3p}$, $R^{4p}$, and $R^{5p}$ may be any non-hydrogen substituent described herein. In other embodiments, $R^{2p}$, $R^{3p}$, $R^{4p}$, and $R^{5p}$ may be any non-hydrogen pyrrole substituent described herein.

In an embodiment, each non-hydrogen group which may be utilized as $R^{2p}$, $R^{3p}$, $R^{4p}$, and/or $R^{5p}$ of Formula P1 and $R^{2i}$, $R^{3i}$, $R^{4i}$, $R^{5i}$, $R^{6i}$, and/or $R^{7i}$ of Formula I1 may independently be an alkyl group, a substituted alkyl group, a cycloalkyl group, a substituted cycloalkyl group, an aromatic group, a substituted aromatic group, an aryl group, a substituted aryl group, an aralkyl group, a substituted aralkyl group, or a silyl group. In other embodiments, each non-hydrogen group which may be utilized as $R^{2p}$, $R^{3p}$, $R^{4p}$, and/or $R^{5p}$ of Formula P1 and $R^{2i}$, $R^{3i}$, $R^{4i}$, $R^{5i}$, $R^{6i}$, and/or $R^{7i}$ of Formula I1 may independently be an alkyl group; alternatively, a substituted alkyl group; alternatively, a cycloalkyl group; alternatively, a substituted cycloalkyl group; alternatively, an aromatic group; alternatively, a substituted aromatic group; alternatively, an aryl group; alternatively, a substituted aryl group; alternatively, an aralkyl group; alternatively, a substituted aralkyl group; or alternatively a silyl group. Generally, the alkyl group, substituted alkyl group, cycloalkyl group, substituted cycloalkyl group, aromatic group, substituted aromatic group, aryl group, substituted aryl group, aralkyl group, substituted aralkyl group, and/or silyl group which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1 may have the same number of carbons as the its respective organyl group, hydrocarbyl group, or silyl group which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1 disclosed herein.

In an embodiment, each alkyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a methyl group, an ethyl group, a propyl group, a butyl group, a pentyl group, a hexyl group, a heptyl group, an octyl group, a nonyl group, a decyl group, a undecyl group, a dodecyl group, a tridecyl group, a tetradecyl group, a pentadecyl group, a hexadecyl group, a heptadecyl group, an octadecyl group, or a nonadecyl group; or alternatively, a methyl group, an ethyl group, a propyl group, a butyl group, a pentyl group, a hexyl group, a heptyl group, an octyl group, a nonyl group, or a decyl group. In some embodiments, each alkyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a methyl group, an ethyl group, a n-propyl group, an iso-propyl group, a n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, a n-propyl group; alternatively, an iso-propyl group; alternatively, a tert-butyl group; or alternatively, a neopentyl group. In an embodiment, any of these alkyl groups may be substituted with a halide, or hydrocarboxy group to form the substituted alkyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1. Substituent halides and hydrocarboxy groups are disclosed herein and may be utilized without limitation to further describe the substituted alkyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1.

In an embodiment, the cycloalkyl group or substituted cycloalkyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, the cycloalkyl group or substituted cycloalkyl group which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1 may be a cyclopentyl group, a substituted cyclopentyl group, a cyclohexyl group, or a substituted cyclohexyl group. In other embodiments, the cycloalkyl group or substituted cycloalkyl group which may be utilized a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1 may be a cyclobutyl group or a substituted cyclobutyl group; alternatively, a cyclopentyl group or a substituted cyclopentyl group; alternatively, a cyclohexyl group or a substituted cyclohexyl group; alternatively, a cycloheptyl group or a substituted cycloheptyl group; or alternatively, a cyclooctyl group, or a substituted cyclooctyl group. In further embodiments, the cycloalkyl group or substituted cycloalkyl group which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1 may be a cyclopentyl group; alternatively, a substituted cyclopentyl group; a cyclohexyl group; or alternatively, a substituted cyclohexyl group. Substituents which may be utilized for the substituted cycloalkyl groups are independently disclosed herein and may be utilized without limitation to further describe the substituted cycloalkyl group which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1.

In an aspect, the aryl group(s) which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a phenyl group, a substituted phenyl group, a naphthyl group, or a substituted naphthyl group. In an embodiment, the aryl group(s) which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a phenyl group or a substituted phenyl group; alternatively, a naphthyl group or a substituted naphthyl group; alternatively, a phenyl group or a naphthyl group; or alternatively, a substituted phenyl group or a substituted naphthyl group. Substituents which may be utilized for the substituted phenyl groups or substituted naphthyl groups are independently disclosed herein and may be utilized without limitation to further describe the substituted phenyl groups or substituted naphthyl groups which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1.

In an embodiment, the substituted phenyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a 2-substituted phenyl group, a 3-substituted phenyl group, a 4-substituted phenyl group, a 2,4-disubstituted phenyl group, a 2,6-disubstituted phenyl group, 3,5-disubstituted phenyl group, or a 2,4,6-trisubstituted phenyl group. In other embodiments, the substituted phenyl group which may be utilized a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, 3,5-disubstituted phenyl group; or alternatively, a 2,4,6-trisubstituted phenyl group. Substituents which may be utilized for these specific substituted phenyl groups are independently disclosed herein and may be utilized without limitation to further describe these substituted phenyl groups which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1.

In an aspect, the aralkyl group(s) which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{4i}$ group of Formula I1 may be a benzyl group, or a substituted benzyl group. In an embodiment, the aralkyl group(s) which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a benzyl group; or alternatively, a substituted benzyl group. Substituents which may be utilized for the substituted aralkyl groups are independently disclosed herein and may be utilized without limitation to further describe the substituted aralkyl groups which may be utilized as a non-hydrogen $R^{2p}$, $R^{3p}$, $R^{4p}$, and/or $R^{5p}$ group of Formula P1 or non-hydrogen $R^{2i}$, $R^{3i}$, $R^{4i}$, $R^{5i}$, $R^{6i}$, and/or $R^{7i}$ group of Formula I1.

In an aspect, the silyl group(s) which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may have Formula Si1. Generally, $R^{1s}$, $R^{2s}$, and $R^{3s}$ of the silyl group having the

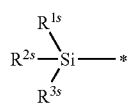

Si1

Formula Si1 may independently be an organyl group or a hydrocarbyl group; alternatively, an organyl group; or alternatively, a hydrocarbyl group. Generally, the organyl group and/or the hydrocarbyl groups which may be utilized as $R^{1s}$, $R^{2s}$, and $R^{3s}$ of the silyl group having the Formula Si1 may have any carbon number as the organyl groups and hydrocarbyl groups which may be utilized as the non-hydrogen pyrrole substituents described herein. In an embodiment, $R^{1s}$, $R^{2s}$, and $R^{3s}$ of the silyl group having the Formula Si1 may independently be an alkyl group, a substituted alkyl group, a cycloalkyl group, a substituted cycloalkyl group, an aromatic group, a substituted aromatic group, an aryl group, a substituted aryl group, an aralkyl group, or a substituted aralkyl group; alternatively, an alkyl group; alternatively, a substituted alkyl group; alternatively, a cycloalkyl group; alternatively, a substituted cycloalkyl group; alternatively, an aromatic group; alternatively, a substituted aromatic group; alternatively, an aryl group; alternatively, a substituted aryl group; alternatively, an aralkyl group; or alternatively, a substituted aralkyl group. Alkyl groups, substituted alkyl groups, cycloalkyl groups, substituted cycloalkyl groups, aromatic groups, substituted aromatic groups, aryl groups, substituted aryl groups, aralkyl groups, and substituted aralkyl groups have been independently described herein as potential non-hydrogen pyrrole substituents and may be utilized, without limitation, as $R^{1s}$, $R^{2s}$, and $R^{3s}$ of the silyl group having the Formula Si1.

In an embodiment, each non-hydrogen substituent(s) for the substituted cycloalkyl group, substituted aromatic group, substituted aryl group, or substituted aralkyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may independently be a halide, a $C_1$ to $C_{10}$ hydrocarbyl group, or a $C_1$ to $C_{10}$ hydrocarboxy group; alternatively, a halide or a $C_1$ to $C_{10}$ hydrocarbyl group; alternatively, a halide or a $C_1$ to $C_{10}$ hydrocarboxy group; alternatively, a $C_1$ to $C_{10}$ hydrocarbyl group or a $C_1$ to $C_{10}$ hydrocarboxy group; alternatively, a halide; alternatively, a $C_1$ to $C_{10}$ hydrocarbyl group; or alternatively, a $C_1$ to $C_{10}$ hydrocarboxy group. In some embodiments, each non-hydrogen substituent(s) for the substituted cycloalkyl group, substituted aromatic group, substituted aryl group, or substituted aralkyl group which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{4i}$ group of Formula I1 may independently be a halide, a $C_1$ to $C_5$ hydrocarbyl group, or a $C_1$ to $C_5$ hydrocarboxy group; alternatively, a halide or a $C_1$ to $C_5$ hydrocarbyl group; alternatively, a halide or a $C_1$ to $C_5$ hydrocarboxy group; alternatively, a $C_1$ to $C_5$ hydrocarbyl group or a $C_1$ to $C_5$ hydrocarboxy group; alternatively, a halide; alternatively, a $C_1$ to $C_5$ hydrocarbyl group; or alternatively, a $C_1$ to $C_5$ hydrocarboxy group. Specific substituent halides, hydrocarbyl groups, and hydrocarboxy groups are independently disclosed herein and may be utilized without limitation to further describe the substituents of the substituted cycloalkyl groups, substituted aromatic groups, substituted aryl groups, or substituted aralkyl groups which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1.

In an embodiment, any halide substituent of a substituted alkyl group (general or specific), substituted cycloalkyl group (general or specific), substituted aromatic group (general or specific), substituted aryl group (general or specific), or substituted aralkyl group may be a fluoride, a chloride, a bromide, or an iodide; alternatively, a fluoride or a chloride. In some embodiments, any halide substituent of a substituted alkyl group (general or specific), substituted cycloalkyl group (general or specific), substituted aromatic group (general or specific), substituted aryl group (general or specific), or substituted aralkyl group may be a fluoride; alternatively, a chloride; alternatively, a bromide; or alternatively, an iodide.

In an embodiment, any hydrocarbyl substituent of a substituted cycloalkyl group (general or specific), substituted aromatic group (general of specific), substituted aryl group (general or specific), or substituted aralkyl group may be an alkyl group, an aryl group, or an aralkyl group; alternatively, an alkyl group; alternatively, an aryl group; or alternatively, an aralkyl group. Generally, the alkyl, aryl, and aralkyl substituent groups may have the same number of carbon atoms as the hydrocarbyl substituent group disclosed herein. In an embodiment, any alkyl substituent of a substituted cycloalkyl group (general or specific), substituted aromatic group (general of specific), substituted aryl group (general or specific), or substituted aralkyl group may be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of a substituted cycloalkyl group (general or specific), substituted aromatic group (general of specific), substituted aryl group (general or specific), or substituted aralkyl group may be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of a substituted cycloalkyl group substituted cycloalkyl group (general or specific), substituted aromatic group (general of specific), substituted aryl group (general or specific), or substituted aralkyl group may be benzyl group.

In an embodiment, any hydrocarboxy substituent of a substituted alkyl group (general or specific), substituted cycloalkyl group (general or specific), substituted aromatic group (general of specific), substituted aryl group (general or specific), or substituted aralkyl group may be an alkoxy group, an aryloxy group, or an aralkoxy group; alternatively, an alkoxy group; alternatively, an aryloxy group; or alternatively, an aralkoxy group. Generally, the alkoxy, aryloxy, and aralkoxy substituent groups may have the same number of carbon atoms as the hydrocarboxy substituent group disclosed herein. In an embodiment, any alkoxy substituent of a substituted alkyl group (general or specific), substituted cycloalkyl group (general or specific), substituted aromatic group (general of specific), substituted aryl group (general or specific), or substituted aralkyl group may be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aroxy substituent of a substituted alkyl group (general or specific), substituted cycloalkyl group (general or specific), substituted aromatic group (general of specific), substituted aryl group (general or specific), or substituted aralkyl group may be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of a substituted alkyl group (general or specific), substituted cycloalkyl group (general or specific), substituted aromatic group (general of specific), substituted aryl group (general or specific), or substituted aralkyl group may be benzoxy group.

In an embodiment, each silyl group(s) which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a trihydrocarbylsilyl group. In some embodiments, each silyl group(s) which may be utilized as a non-hydrogen $R^{2p}$, $R^{3p}$, $R^{4p}$, and/or $R^{5p}$ group of Formula P1 or a non-hydrogen $R^{2i}$, $R^{3i}$, $R^{4i}$, $R^{5i}$, $R^{6i}$, and/or $R^{7i}$ group of Formula I1 may be a trialkylsilyl group, a triphenylsilyl group, or a tri(substituted phenyl)silyl group; alternatively, a trialkylsilyl group; alternatively, a triphenylsilyl group; or alternatively, a tri(substituted phenyl)silyl group. Hydrocarbyl groups, alkyl groups, and substituted phenyl groups have been independently described herein as potential non-hydrogen pyrrole substituents and may be utilized, without limitation, as $R^{1s}$, $R^{2s}$, and $R^{3s}$ of the silyl group having the Formula Si1.

In an embodiment, the pyrrole compound may comprise, consist essentially of, or consist of, a pyrrole compound having a $C_1$ to $C_{18}$ group attached to the 2- and 5-positions of the pyrrole. Unless otherwise specified, the pyrrole compound having a $C_1$ to $C_{18}$ group attached to the 2- and 5-positions, may have groups attached at the 1, 3, and/or 4 positions. In an embodiment, the pyrrole compound of the oligomerization catalyst system can be a 2,5-disubstituted pyrrole compound, that is, the pyrrole compound has substituents only at the 2- and 5-positions. Regardless of whether or not the pyrrole compound has substituents present at the 1, 3, and/or 4 positions, the groups attached to the 2- and 5-positions of the pyrrole compound may be the same or different. For example, 2,5-dimethylpyrrole, 2-ethyl-5-methylpyrrole and 2-ethyl-5-propyl pyrrole are among the suitable 2,5-disubstituted pyrroles for use in the catalyst system and methods of this disclosure. In other aspects and embodiments, the groups attached to the 2- and 5-positions of the pyrrole compound may be the same. Generally, the groups attached to the 2- and 5-position of the pyrrole compound may be any pyrrole substituent group disclosed herein.

In a particular non-limiting embodiment, the pyrrole compound may have $C_2$ to $C_{18}$ organyl groups attached at the 2- and 5-positions of the pyrrole ring. In other embodiments, the groups attached at the 2- and 5-positions of the pyrrole ring may independently be $C_2$ to $C_{12}$ organyl groups; or alternatively, $C_2$ to $C_8$ organyl groups. In other particular non-limiting embodiments, the groups attached at the 2- and 5-positions of the pyrrole ring may independently be $C_2$ to $C_{18}$ hydrocarbyl groups; alternatively, $C_2$ to $C_{12}$ hydrocarbyl groups; or alternatively, a $C_2$ to $C_8$ hydrocarbyl groups. In yet other particular non-limiting embodiments, the groups attached at the 2- and 5-positions of the pyrrole ring may independently be $C_2$ to $C_{18}$ alkyl groups; alternatively, $C_2$ to $C_{12}$ alkyl groups; or alternatively, a $C_2$ to $C_8$ alkyl groups.

In an aspect the groups attached to the 2- and 5-positions of the pyrrole ring are attached to the pyrrole ring in such a way that at least one carbon atom attached to the 2- and 5-positions of the pyrrole ring is a secondary carbon atom; alternatively, the groups attached to the 2- and 5-positions of the pyrrole ring are attached to the pyrrole ring in such a way that both the carbon atoms attached to the 2- and 5-positions of the pyrrole ring are secondary carbon atoms. That is, when the carbon atom of the group attached to the pyrrole ring is a secondary carbon atom, that secondary carbon is attached to one, and only one, other carbon atom besides the carbon atom of the pyrrole ring. In some embodiments, the groups attached to the 2- and 5-positions are attached in such a way that the carbon atoms attached to the 2- and 5-positions of the pyrrole ring are secondary carbon atoms, and the groups are branched. In other embodiments the groups attached to the 2 and 5 position of the pyrrole ring may be linear. In an embodiment, an ethylene trimerization process utilizing a catalyst system utilizing a pyrrole compound comprising or consisting of groups attached to the 2- and 5-positions of the pyrrole ring and wherein the groups attached to the 2- and/or 5-positions are attached to the pyrrole ring in such a way that at least one carbon atom attached to the 2- and 5-positions of the pyrrole ring is a secondary carbon atom may provide a higher selectivity to 1-hexene than the process using 2,5-dimethylpyrrole as the pyrrole compound and/or provides a higher purity 1-hexene product than the process using 2,5-dimethylpyrrole as the pyrrole compound. In another embodiment, an ethylene trimerization process utilizing a catalyst system utilizing a pyrrole compound comprising or consisting of groups attached to the 2- and 5-positions of the pyrrole ring and wherein the groups attached to the 2- and/or 5-positions are attached to the pyrrole ring in such a way that at least one carbon atom attached to the 2- and 5-positions of the pyrrole ring is a secondary carbon atom may provide a higher selectivity to 1-hexene than the process using 2,5-dimethylpyrrole as the pyrrole compound and/or provides a higher purity 1-hexene product than the process using 2,5-dimethylpyrrole as the pyrrole compound.

In an embodiment wherein the carbon atom of the either of the groups attached to 2- and 5-position of the pyrrole ring is a secondary carbon atom, the groups attached to 2-position and/or the 5-position may independently be an ethyl group, a n-propyl group, a n-butyl group, a n-pentyl group, a n-hexyl group, a n-heptyl group, or a n-octyl group; alternatively, an ethyl group, a n-propyl group, a n-butyl group, or a n-pentyl group; alternatively, an ethyl group; alternatively, a n-propyl group; alternatively, a n-butyl group; alternatively, a n-pentyl group; alternatively, a n-hexyl group; alternatively, a n-heptyl group; or alternatively, a n-octyl group. For example, the pyrrole compound may be a 2,5-disubstituted pyrrole, such as 2,5-diethyl pyrrole.

In an aspect, the pyrrole can have the formula P1 wherein $R^{2p}$ and $R^{5p}$ independently are any group disclosed herein and wherein at least one of the groups attached to the 2- and 5-positions is attached in a manner wherein the carbon atom attached to the pyrrole ring is a secondary carbon atom and $R^{3p}$ and $R^{4p}$ independently are hydrogen and any non-hydrogen pyrrole substituent disclosed herein; alternatively, $R^{2p}$ and $R^{5p}$ independently are any group disclosed herein and wherein at least one of the groups attached to the 2- and 5-positions is attached in a manner wherein the carbon atom attached to the pyrrole ring is a secondary carbon atom and $R^{3p}$ and $R^{4p}$ are hydrogen. In another aspect, $R^{2p}$ and $R^{5p}$ independently are any group disclosed herein each of the groups attached to the 2- and 5-positions is attached in a manner wherein the carbon atom attached to the pyrrole ring is a secondary carbon atom and $R^{3p}$ and $R^{4p}$ independently are hydrogen and any non-hydrogen pyrrole substituent disclosed herein; alternatively, $R^{2p}$ and $R^{5p}$ independently are any group disclosed herein wherein the groups attached to the 2- and 5-positions is attached in a manner wherein the carbon atom attached to the pyrrole ring are secondary carbon atoms and $R^{3p}$ and $R^{4p}$ are hydrogen.

In some non-limiting embodiments wherein the groups attached to the 2- and 5-positions are attached in such a manner that at least one (or alternatively both) of the carbon atoms attached to the pyrrole ring are secondary carbons, the pyrrole compound may be a 2,5-dialkylpyrrole, a 2,3,5-triialkylpyrrole, a 2,4,5-triialkylpyrrole, a 2,3,4,5-tetraalkylpyrrole, or any combination thereof; alternatively, a 2,5-dialkylpyrrole; alternatively, a 2,3,5-triialkylpyrrole; alternatively, a 2,4,5-triialkylpyrrole; or alternatively, a 2,3,4,5-tetraalkylpyrrole.

In some non-limiting embodiments wherein the groups attached to the 2- and 5-positions are attached in such a manner that at least one (or alternatively both) of the carbon atoms attached to the pyrrole ring are secondary carbons, the pyrrole compound may be 2-methyl-5-ethylpyrrole, 2,5-diethylpyrrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, 2,3,5-triethylpyrrrole, 2,3,5-tri-n-butylpyrrrole, 2,3,5-tri-n-pentylpyrrrole, 2,3,5-tri-n-hexylpyrrrole, 2,3,5-tri-n-heptylpyrrrole, 2,3,5-tri-n-octylpyrrrole, 2,3,4,5-tetraethylpyrrole, 2,3,4,5-tetra-n-butylpyrrole, 2,3,4,5-tetra-n-hexylpyrrole, 2,5-bis(2',2',2'-trifluoroethyl)pyrrole, 2,5-bis(2'-methoxymethyl)pyrrole, or any combination thereof; alternatively, 2-methyl-5-ethylpyrrole, 2,5-diethylpyrrrole, 2,5-di-n-propylpyrrole, 2,5-di-n-butylpyrrole, 2,5-di-n-pentylpyrrole, 2,5-di-n-hexylpyrrole, 2,5-di-n-heptylpyrrole, 2,5-di-n-octylpyrrole, or any combination thereof; alternatively, 2-methyl-5-ethylpyrrole; alternatively, 2,5-diethylpyrrrole; alternatively, 2,5-di-n-propylpyrrole; alternatively, 2,5-di-n-butylpyrrole; alternatively, 2,5-di-n-pentylpyrrole; alternatively, 2,5-n-hexylpyrrole; alternatively, 2,5-di-n-heptylpyrrole; or alternatively, 2,5-di-n-octylpyrrole.

In an aspect, the pyrrole compound may have a hydrogen atom located on at least one pyrrole ring carbon atom adjacent to the nitrogen atom of the pyrrole ring and a bulky group located on a pyrrole ring carbon atom adjacent to any pyrrole ring carbon atom bearing the hydrogen atom adjacent to the nitrogen atom of the pyrrole ring; alternatively, has a hydrogen atom located on each pyrrole ring carbon atom adjacent to the nitrogen atom of the pyrrole ring and bulky group located on each pyrrole ring carbon atom adjacent to the pyrrole ring carbon atoms bearing the hydrogen atom adjacent to the nitrogen atom of the pyrrole ring. Generally, each group in this aspect may be any group described herein and have any number of carbons described herein that meets the requirements of the pyrrole compound. For example, any non-hydrogen pyrrole group located on a pyrrole ring carbon atom adjacent to the pyrrole ring nitrogen atom and any non-hydrogen pyrrole group located on a pyrrole ring carbon atom adjacent to a pyrrole ring carbon atom bearing an non-hydrogen pyrrole group on a pyrrole ring carbon atom adjacent to the pyrrole ring nitrogen atom may be any $C_1$ to $C_{18}$, $C_1$ to $C_{15}$, $C_1$ to $C_{10}$, or $C_1$ to $C_5$ organyl group (alternatively any hydrocarbyl group) described herein while the group located on a pyrrole ring carbon atom adjacent to a the pyrrole ring carbon atom bearing the hydrogen atom that is adjacent to the nitrogen atom of the pyrrole ring may be any bulky $C_3$ to $C_{18}$, $C_3$ to $C_{15}$, $C_3$ to $C_{10}$, or $C_3$ to $C_5$ organyl group (alternatively any hydrocarbyl group) described herein. In an aspect, each bulky substituent may be a triorganylsilyl group; or alternatively, a trihydrocarbylsilyl group. Generally, the triorganylsilyl and/or the trihydrocarbylsilyl group may have the same number of carbon atoms as the silyl group which may be utilized as a pyrrole substituent described herein. In an embodiment, each bulky substituent may be a trialkylsilyl group, a triphenylsilyl group, or a tri(substituted phenyl)silyl group; alternatively, a trialkylsilyl group; alternatively, a triphenylsilyl group; or alternatively, a tri(substituted phenyl) silyl group.

In an aspect, the pyrrole compound may be a pyrrole compound having Formula P2, Formula P3, Formula P4, or a combination thereof; alternatively, Formula P2; alternatively, Formula P3; alternatively Formula P4. In an embodiment, $R^{12p}$ and $R^{13p}$ of

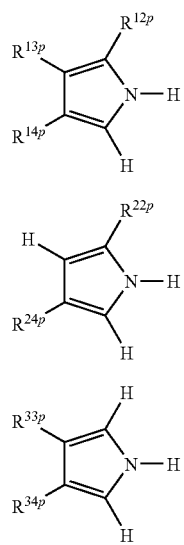

Formula P2 and $R^{22p}$ of Formula P3 may be any pyrrole substituent group disclosed herein while $R^{14p}$ of Formula P2, $R^{24p}$ of Formula P3, and $R^{33p}$ and $R^{34p}$ of Formula P4 may be any bulky pyrrole substituent disclosed herein. For example, $R^{12p}$ and $R^{13p}$ of Formula P2 and $R^{23p}$ of Formula P3 may be any $C_1$ to $C_{18}$, $C_1$ to $C_{15}$, $C_1$ to $C_{10}$, or $C_1$ to $C_5$ organyl group (alternatively, any hydrocarbyl group) described herein while $R^{14p}$ of Formula P2, $R^{22p}$ of Formula P3, and $R^{33p}$ and $R^{34p}$ of Formula P4 may be any bulky $C_3$ to $C_{18}$, $C_3$ to $C_{15}$, $C_3$ to $C_{10}$, or $C_3$ to $C_5$ organyl group (alternatively, any hydrocarbyl group) described herein. In an aspect, each bulky substituent may be a triorganylsilyl group; or alternatively, a trihydrocarbylsilyl group.

In an embodiment, the bulky pyrrole substituent may be defined as one wherein the carbon atom of bulky group that is attached to the pyrrole ring carbon atom is a tertiary or quaternary carbon atom or one wherein the carbon atom of the bulky group that is adjacent to the carbon atom attached to pyrrole ring carbon atom is a tertiary or quaternary carbon atom; alternatively one wherein the carbon atom of bulky group that is attached to the pyrrole ring carbon atom is a tertiary or quaternary carbon atom; or alternatively one wherein the carbon atom of the bulky group that is adjacent to the carbon atom attached to pyrrole ring carbon atom is a tertiary or quaternary carbon atom. In some embodiments, the bulky pyrrole substituent may be defined as one wherein the carbon atom of bulky group that is attached to the pyrrole ring carbon atom is a tertiary carbon atom or one wherein the carbon atom of the bulky group that is adjacent to the carbon atom attached to pyrrole ring carbon atom is a tertiary carbon atom; alternatively one wherein the carbon atom of bulky group that is attached to the pyrrole ring carbon atom is a tertiary carbon atom; or alternatively one wherein the carbon atom of the bulky group that is adjacent to the carbon atom attached to pyrrole ring carbon atom is a tertiary carbon atom. In other embodiments, the bulky pyrrole substituent may be defined as one wherein the carbon atom of bulky group that is attached to the pyrrole ring carbon atom is a quaternary carbon atom or one wherein the carbon atom of the bulky group that is adjacent to the carbon atom attached to pyrrole ring carbon atom is a quaternary carbon atom; alternatively one wherein the carbon atom of bulky group that is attached to the pyrrole ring carbon atom is a quaternary carbon atom; or alternatively one wherein the carbon atom of the bulky group that is adjacent to the carbon atom attached to pyrrole ring carbon atom is a quaternary carbon atom. In an embodiment, a bulky silyl group is one wherein the silicon atom of the bulky silyl group attached to the pyrrole ring carbon is attached to four carbon atoms.

In an embodiment, the bulky pyrrole substituent may be defined as one wherein the carbon atom of bulky group that is attached to the pyrrole ring carbon atom is attached to 3 or 4 carbon atoms or one wherein the carbon atom of the bulky group that is adjacent to the carbon atom attached to pyrrole ring carbon atom is attached to 3 or 4 carbon atoms; alternatively one wherein the carbon atom of bulky group that is attached to the pyrrole ring carbon atom is attached to 3 or 4 carbon atoms; or alternatively, one wherein the carbon atom of the bulky group that is adjacent to the carbon atom attached to pyrrole ring carbon atom is attached to 3 or 4 carbon atoms. In some embodiments, the bulky pyrrole substituent may be defined as one wherein the carbon atom of bulky group that is attached to the pyrrole ring carbon atom is attached to 3 carbon atoms or one wherein the carbon atom of the bulky group that is adjacent to the carbon atom attached to pyrrole ring carbon atom is attached to 3 carbon atoms; alternatively one wherein the carbon atom of bulky group that is attached to the pyrrole ring carbon atom is attached to 3 carbon atoms; or alternatively one wherein the carbon atom of the bulky group that is adjacent to the carbon atom attached to pyrrole ring carbon atom is attached to 3 carbon atoms. In other embodiments, the bulky pyrrole substituent may be defined as one wherein the carbon atom of bulky group that is attached to the pyrrole ring carbon atom is attached to 4 carbon atoms or one wherein the carbon atom of the bulky group that is adjacent to the carbon atom attached to pyrrole ring carbon atom is attached to 4 carbon atoms; alternatively one wherein the carbon atom of bulky group that is attached to the pyrrole ring carbon atom is attached to 4 carbon atoms; or alternatively one wherein the carbon atom of the bulky group that is adjacent to the carbon atom attached to pyrrole ring carbon atom is attached to 4 carbon atoms.

For illustration purposes, Formula E1 is used to illustrate the carbon atom attached to the pyrrole ring and the carbon atom adjacent to the carbon atom attached to the pyrrole ring carbon atom.

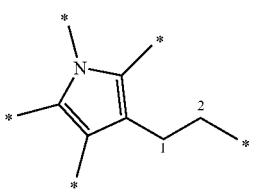

Using Formula E1, the carbon atom labeled 1 within the group attached to the pyrrole ring represents the carbon atom attached to the pyrrole ring carbon atom while the carbon atom labeled 2 within the group attached to the pyrrole ring represents the carbon atom adjacent to the carbon atom attached to the pyrrole ring carbon atom. In an embodiment, a bulky silyl group is one wherein the silicon atom of the bulky silyl group attached to the pyrrole ring carbon is attached to four carbon atoms.

In an embodiment, the bulky substituent may independently be an alkyl group, a substituted alkyl group, a cycloalkyl group, a substituted cycloalkyl group, an aromatic group, a substituted aromatic group, an aryl group, a substituted aryl group, an aralkyl group, a substituted aralkyl group, or a silyl group. Generally, the alkyl group, a substituted alkyl group, a cycloalkyl group, a substituted cycloalkyl group, an aromatic group, a substituted aromatic group, an aryl group, a substituted aryl group, an aralkyl group, a substituted aralkyl group, and silyl group which may be utilized as the bulky substituent may have the same number of carbon atoms as the bulky organyl (or hydrocarbyl)pyrrole substituent disclosed herein. Alkyl groups, substituted alkyl groups, cycloalkyl groups, substituted cycloalkyl groups, aromatic groups, substituted aromatic groups, aryl groups, substituted aryl groups, aralkyl groups, substituted aralkyl groups, and silyl groups are generally disclosed herein and those that meet the criteria for a bulky substituent may be utilized, without limitation to further describe the pyrrole compound which may be utilized in some aspect and embodiments disclosed herein.

In an embodiment, each bulky substituent may independently be a propan-2-yl group, a butan-2-yl, a 2-methylpropan-1-yl group, a 2-methylpropan-2-yl group, a pentan-2-yl group, a pentan-3-yl group, a 2-methylbutan-1-yl group, a 2-methylbutan-2-yl group, a 3-methylbutan-2-yl group, 2,2-dimethylpropan-1-yl group, a hexan-2-yl group, a hexan-3-yl group, a 2-methylpentan-1-yl group, 2-ethylbutan-1-yl group, a 2-methylpentan-2-yl group, a 2,3-dimethylbutan-1-yl group, a 2,3-dimethylbutan-2-yl group, a heptan-2-yl group, a heptan-3-yl group, a heptan-4-yl group, a 2-methylhexan-1-yl group, a 2-ethylpentan-1-yl group, a 2-methylhexan-2-yl group, a 2,3-dimethylpentan-1-yl group, a 2,3-dimethylpentan-2-yl group, a 2,3,3-trimethylpentan-1-yl group, a 2,3,3-trimethylpentan-2-yl group, an octan-2-yl group, an octan-3-yl group, an octan-4-yl group, a 2-methylheptan-1-yl group, a 2-ethylhexan-1-yl group, a 2-methylheptan-2-yl group, a nonan-2-yl group, a nonan-3-yl group, a nonan-4-yl group, a nonan-5-yl group, a decan-2-yl group, a decan-3-yl group, a decan-4-yl group, or a decan-5-yl group. In other embodiments, each bulky substituent may independently be a propan-2-yl group, a butan-2-yl, a 2-methylpropan-1-yl group, a 2-methylpropan-2-yl group, a pentan-2-yl group, a pentan-3-yl group, a 2-methylbutan-1-yl group, a 2-methylbutan-2-yl group, a 3-methylbutan-2-yl group, 2,2-dimethylpropan-1-yl group; alternatively, propan-2-yl group, a 2-methylpropan-2-yl group, or a 2,2-dimethylpropan-1-yl group. In other embodiments, each bulky substituent may independently be a propan-2-yl group; alternatively, a butan-2-yl; alternatively, a 2-methylpropan-1-yl group; alternatively, a 2-methylpropan-2-yl group; alternatively, a pentan-2-yl group; alternatively, a pentan-3-yl group; alternatively, a 2-methylbutan-1-yl group; alternatively, a 2-methylbutan-2-yl group; alternatively, a 3-methylbutan-2-yl group; alternatively, 2,2-dimethylpropan-1-yl group.

In an aspect, each bulky substituent may independently be a phenyl group or a substituted phenyl group; alternatively, a phenyl group; or alternatively, a substituted phenyl group. In an embodiment, the substituted phenyl group which may be utilized as a bulky substituent may be a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, or a 2,4,6-tripheneyl group. In some embodiments, the substituted phenyl group which may be utilized as a bulky substituent may be a 2-methylphenyl group, a 2,4-dimethylphenyl group, a 2,6-dimethylphenyl group, a 3,5-dimethylphenyl group, or a 2,4,6-tripheneyl group. In other embodiments, the substituted phenyl group which may be utilized as a bulky substituent may be a 2-methylphenyl group; alternatively, a 3-methylphenyl group; alternatively, a 4-methylphenyl group; alternatively, a 2,3-dimethylphenyl group; alternatively, a 2,4-dimethylphenyl group; alternatively, a 2,5-dimethylphenyl group; alternatively, a 2,6-dimethylphenyl group; alternatively, a 3,4-dimethylphenyl group; alternatively, a 3,5-dimethylphenyl group; or alternatively, a 2,4,6-tripheneyl group.

In another aspect, each bulky substituent may independently be a trimethylsilyl group, a triethylsilyl group, a triisopropylsilyl group, a tri-t-butylsilyl group, or a triphenylsilyl group; alternatively, a trimethylsilyl group, a triethylsilyl group, a triisopropylsilyl group, or a tri-t-butylsilyl group. In an embodiment, each bulky substituent may be a trimethylsilyl group; alternatively, a triethylsilyl group; alternatively, a triisopropylsilyl group; alternatively, a tri-t-butylsilyl group; or alternatively, a triphenylsilyl group.

In a non-limiting example, the pyrrole compound may be 2-methyl-4-isopropylpyrrole, 2-ethyl-4-isopropylpyrrole, 2-methyl-4-sec-butylpyrrole, 2-ethyl-4-sec-butylpyrrole, 2-methyl-4-isobutylpyrrole, 2-ethyl-4-isobutylpyrrole, 2-methyl-4-t-butylpyrrole, 2-ethyl-4-t-butylpyrrole, 2-methyl-4-neo-pentylpyrrole, or 2-ethyl-4-neopentylpyrrole. In some non-limiting examples, the pyrrole compound may be 2-methyl-4-isopropylpyrrole, 2-ethyl-4-isopropylpyrrole, 2-methyl-4-t-butylpyrrole, 2-ethyl-4-t-butylpyrrole, 2-methyl-4-neo-pentylpyrrole, or 2-ethyl-4-neopentylpyrrole. In other non-limiting examples, the pyrrole compound may be 2-methyl-4-isopropylpyrrole; alternatively, 2-ethyl-4-isopropylpyrrole; alternatively, 2-methyl-4-sec-butylpyrrole; alternatively, 2-ethyl-4-sec-butylpyrrole; alternatively, 2-methyl-4-isobutylpyrrole; alternatively, 2-ethyl-4-isobutylpyrrole; alternatively, 2-methyl-4-t-butylpyrrole; alternatively, 2-ethyl-4-t-butylpyrrole; alternatively, 2-methyl-4-neo-pentylpyrrole; or alternatively, 2-ethyl-4-neopentylpyrrole. In another non-limiting example, the pyrrole compound may be 3,4-diisopropylpyrrole, 3,4-di-sec-butylpyrrole, 3,4-diisobutylpyrrole, 3,4-di-t-butylpyrrole, or 3,4-di-neo-pentylpropylpyrrole. In yet another embodiment, the pyrrole compound may be 3,4-diisopropylpyrrole: alternatively, 3,4-di-sec-butylpyrrole; alternatively, 3,4-diisobutylpyrrole; alternatively, 3,4-di-t-butylpyrrole; or alternatively, 3,4-di-neo-pentylpropylpyrrole Metal Alkyl Generally, and according to one aspect of this disclosure, the metal alkyl may be any heteroleptic or homoleptic metal alkyl compound. For example, the metal of the metal alkyl can comprise, consist essentially of, or consist of, Group 1, 2, 11, 12, 13, or 14 metal; or alternatively, a Group 13 or 14 metal; or alternatively, a Group 13 metal. In some embodiments and aspects, the metal alkyl may comprise, consist essentially of, or consist of, a lithium alkyl, sodium alkyl, magnesium alkyl, boron alkyl, a zinc alkyl, or an aluminum alkyl. In this aspect, for example, suitable metal alkyls include, but are not limited to, n-butyl lithium, sec-butyl lithium, tert-butyl lithium, diethyl magnesium, or diethyl zinc. In an embodiment the metal alkyl may comprise, consist essentially of, or consist of, an aluminum alkyl.

According to a further aspect and in any embodiment of this disclosure, the metal alkyl may comprise a metal alkyl halide. Metal alkyl halides are described herein and may be utilized as the metal alkyl component of the oligomerization catalyst system. The halide portion of the metal alkyl halide may be chloride; alternatively bromide; or alternatively iodide.

In some aspects and embodiments according to this disclosure, the metal alkyl can be a non-hydrolyzed alkyl aluminum compound. In an embodiment, the non-hydrolyzed alkyl aluminum compound may be a trialkyl aluminum compound, an alkyl aluminum halide, or and alkyl aluminum alkoxide.

Generally, each alkyl group of any metal alkyl described herein (e.g. alkyl aluminum compound or alkylaluminum halide, among others), if there is more than one, may independently be a $C_1$ to $C_{20}$ alkyl group; alternatively, a $C_1$ to $C_{10}$ alkyl group; or alternatively, a $C_1$ to $C_6$ alkyl group. In an embodiment, each alkyl group(s) may independently be a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some embodiments, each alkyl group of any metal alkyl described herein may independently be a methyl group, an ethyl group, an n-propyl group, an n-butyl group, an iso-butyl group, a n-hexyl group, or an n-octyl group; alternatively, a methyl group, an ethyl group, a n-butyl group, or an iso-butyl group; alternatively, a methyl group; alternatively, an ethyl group; alternatively, an n-propyl group; alternatively, an n-butyl group; alternatively, an iso-butyl group; alternatively, a n-hexyl group; or alternatively, an n-octyl group.

According to another aspect of this disclosure, the metal alkyl can comprise, consist essentially of, or consist of, a trialkylaluminum compound, a dialkylaluminum halide compound, an alkylaluminum dihalide compound, a dialkylaluminum hydride compound, an alkylaluminum dihydride compound, a dialkylaluminum hydrocarboxide compound, an alkylaluminum dihydrocarboxide compound, an alkyl aluminum sesquihalide compound, an alkylaluminum sesquihydrocarboxide compound, an aluminoxane, or any combination thereof. In some embodiments, the metal alkyl can comprise, consist essentially of, or consist of, a trialkylaluminum compound, dialkylaluminum halide compound, an alkylaluminum dihalide compound, or any combination thereof; alternatively, a trialkylaluminum compound; alternatively, a dialkylaluminum halide compound; alternatively, an alkylaluminum dihalide compound; alternatively, a dialkylaluminum hydride compound; alternatively, an alkylaluminum dihydride compound; alternatively, a dialkylaluminum hydrocarboxide compound; alternatively, an alkylaluminum dihydrocarboxide compound; alternatively, an alkylaluminum sesquihalide compound; alternatively, an alkylaluminum sesquihydrocarboxide compound; or alternatively, an aluminoxane. Applicable alkyl groups and halides for the metal alkyl, metal alkyl halides, and/or metal alkyl hydrocarboxides are described herein and may be utilized to further describe the suitable metal alkyls.

Exemplary trialkyl aluminum compounds include but are not limited to, trimethylaluminum (TMA), triethylaluminum (TEA), tripropylaluminum, tri-n-butylaluminum, or tri-isobutylaluminum, or mixtures thereof. Exemplary alkylaluminum halide compounds may include, but are not limited to, diethylaluminum chloride (DEAC), diethylaluminum bromide, ethylaluminum dichloride, ethylaluminum sesquichloride, and mixtures thereof. In various embodiments, the trialkylaluminum compound may be triethylaluminum.

According to a further aspect, the metal alkyl compound may comprise, consist essentially of, or consist of, a mixture of a trialkylaluminum compound and an alkylaluminum halide. Generally, the trialkylaluminum compound of the mixture may comprise, consist essentially of, or consist of, any trialkylaluminum compound described herein. The alkylaluminum halide compound of the mixture may be any alkylaluminum compound described herein. In some embodiments, the mixture of the trialkylaluminum compound and the alkylaluminum halide may comprise, consist essentially of, or consist of, a mixture of triethylaluminum and diethylaluminum chloride, a mixture of triethylaluminum and ethylaluminum dichloride, or a mixture of triethylaluminum and ethylaluminum sesquichloride. In an embodiment, the metal alkyl component of the oligomerization catalyst system may comprise, consist essentially of, or consist of, a mixture of triethylaluminum and diethylaluminum chloride.

In another aspect and in any embodiments, specific examples of metal alkyls that are useful in this disclosure may comprise, consist essentially of, or consist of, but are not limited to, trimethylaluminum (TMA), triethylaluminum (TEA), ethylaluminum dichloride, tripropylaluminum, diethylaluminum ethoxide, tributylaluminum, disobutylaluminum hydride, triisobutylaluminum, diethylaluminum chloride (DEAC), and combinations thereof. In other aspects, and in any embodiments, specific examples of metal alkyls that are useful in this disclosure can comprise or can include, but are not limited to triethylaluminum (TEA), diethylaluminum chloride (DEAC), or any combination thereof.

In a non-limiting embodiment, useful aluminoxanes may have a repeating unit of Formula I:

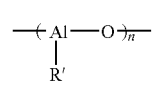

Formula I wherein R' is a linear or branched alkyl. Alkyl groups for metal alkyls have been independently described herein and may be utilized without limitation to further describe the aluminoxanes having Formula I. Generally, n of Formula I is greater than 1; or alternatively greater than 2. In an embodiment, n may be range from 2 to 15; or alternatively, range from 3 to 10.

In a non-limiting embodiment, useful aluminoxanes which may be utilized in the catalyst system may comprise, consist essentially of, or consist of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-pentylaluminoxane, 3-pentylaluminoxane, iso-pentylaluminoxane, neopentylaluminoxane, or mixtures thereof. In some non-limiting embodiments, aluminoxanes may comprise, consist essentially of, or consist of, methylaluminoxane (MAO), modified methylaluminoxane (MMAO), isobutyl aluminoxane, t-butylaluminoxane, or mixtures thereof. In other non-limiting embodiments, useful aluminoxanes may be methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butylaluminoxane; alternatively, 1-pentylaluminoxane; alternatively, 2-pentylaluminoxane; alternatively, 3-pentyl-aluminoxane; alternatively, iso-pentylaluminoxane; or alternatively, neopentylaluminoxane.

Halogen Containing Compound

While not intending to be bound by theory, it is thought that a halogen containing compound can improve product purity and/or selectivity of the oligomerization process. In some aspects and embodiments, the halogen containing compound may be a chloride containing compound, a bromide containing compound, or an iodide containing compound. In an embodiment, the halogen containing compound may be a chloride containing compound.

In an aspect, the halogen containing compound, regardless of whether it is a chloride, bromide, or iodide containing compound, may be a metal halide, alkyl metal halide, or an organic halide. In various embodiments and aspect, the halogen containing compound may be a metal chloride; alternatively, a metal bromide; or alternatively, a metal iodide. In an embodiment, the halogen containing compound may be a metal alkyl chloride; alternatively, a metal alkyl bromide; or alternatively, a metal iodide. In an embodiment, the halogen containing compound may be an organic chloride; alternatively, an organic bromide; or alternatively, an organic iodide.

Moreover, and in another aspect, the halogen containing compound comprises a group 3 metal halide, a group 4 metal halide, a group 5 metal halide, a group 13 metal halide, a group 14 metal halide, a group 15 metal halide, or any combination thereof. By way of example, the halogen containing compound can be or the halogen containing compound can comprise scandium chloride, yttrium chloride, lanthanum chloride, titanium tetrachloride, zirconium tetrachloride, hafnium tetrachloride, boron trichloride, aluminum chloride, gallium chloride, silicon tetrachloride, trimethyl chlorosilane, germanium tetrachloride, tin tetrachloride, phosphorus trichloride, antimony trichloride, antimony pentachloride, bismuth trichloride, boron tribromide, aluminum tribromide, silicon tetrachloride, silicon tetrabromide, aluminum fluoride, molybdenum pentachloride, tungsten hexachloride, trityl hexachloroantimonate, or any combination thereof.

In accordance with another aspect, the halogen containing compound may comprise, consist essentially of, or consist of, a Group 1, 2, 12, or 13 alkyl metal halide; alternatively, a Group 12 or 13 alkyl metal halide; or alternatively, an alkylaluminum halide or an alkyltin halide. According to a further aspect, the halogen containing compound may comprise, consist essentially of, or consist of, an alkylaluminum halide. In some embodiment, the alkylaluminum halide may be an alkylaluminum chloride; alternatively, an alkylaluminum bromide; or alternatively, and alkylaluminum iodide. In other embodiments, the alkyltin halide may be an alkyltin chloride; alternatively, an alkyltin bromide; or alternatively, an alkyltin iodide. In an embodiment, the alkyl metal halide may be an alkylaluminum halide. In another embodiment, the alky metal halide may be an alkyltin halide.

In various embodiments and according to another aspect, the halogen containing compound can comprise, consist essentially of, or consist of, a dialkylaluminum halide, an alkylaluminum dihalide, or an alkylaluminum sesquihalide, or any combination thereof; alternatively, a dialkylaluminum halide; alternatively, an alkylaluminum dihalide; or alternatively, an alkylaluminum sesquihalide. In this aspect, the alkyl group of the alkylaluminum halide, the alkyltin halide, the dialkylaluminum halide, the alkylaluminum dihalide, or the alkylaluminum sesquihalide may be a $C_1$ to $C_8$ alkyl group. Moreover and in this aspect, the halogen containing compound can comprise, consist essentially of, or consist of, diethylaluminum chloride, ethylaluminum sesquichloride, ethylaluminum dichloride, tributyltin chloride, dibutyltin dichloride, or any combination thereof; alternatively, diethylaluminum chloride, ethylaluminum sesquichloride, ethylaluminum dichloride, or any combination thereof; or alternatively, diethylaluminum chloride; alternatively, ethylaluminum sesquichloride; or alternatively, ethylaluminum dichloride.

According to a further aspect and in any embodiment, the halogen containing compound can comprise a $C_1$ to $C_{15}$ organic halide; alternatively, a $C_1$ to $C_{10}$ organic halide; or alternatively, a $C_1$ to $C_8$ organic halide. By way of example, according to this aspect, the halogen containing compound can comprise, consist essentially of, or consist of, carbon tetrachloride, carbon tetrabromide, chloroform, bromoform, dichloromethane, dibromoethane, diiodomethane, chloromethane, bromomethane, iodomethane, dichloroethane, tetrachloroethane, trichloroacetone, hexachloroacetone, hexachlorocyclohexane, 1,3,5-trichlorobenzene, hexachlorobenzene, trityl chloride, benzyl chloride, benzyl bromide, benzyl iodide, chlorobenzene, bromobenzene, iodobenzene, hexafluorobenzene, or any combination thereof.

In an aspect, the catalyst system may have a molar ratio of metal in the transition metal compound to metal in the metal alkyl ranging from 1:1 to 1:150; alternatively, 1:1 to 1:100; or alternatively, 1:9 to 1:21. In an embodiment, when the transition metal compound is a chromium compound (e.g. a chromium(III) carboxylate composition) and the metal alkyl is an alkylaluminum compound (e.g. triethylaluminum, diethylaluminum chloride, or a mixture thereof), the catalyst system may have a molar ratio of chromium to aluminum ranging from 1:1 to 1:150; alternatively, 1:1 to 1:100; or alternatively, 1:9 to 1:21.

In an aspect, the catalyst system may have a molar ratio of nitrogen of the pyrrole compound to metal of the transition metal compound ranging from 1.0:1 to 4.0:1; alternatively from 1.5:1 to 3.7:1; alternatively from 1.5:1 to 2.5:1; alternatively from 2.0:1 to 3.7:1; alternatively from 2.5:1 to 3.5:1; or alternatively from 2.9:1 to 3.1:1. In an embodiment when the transition metal compound is a chromium compound (e.g. a chromium(III) carboxylate composition) the molar ratio of chromium to pyrrole may range from 1.0:1 to 4.0:1; alternatively from 1.5:1 to 3.7:1; alternatively from 1.5:1 to 2.5:1; alternatively from 2.0:1 to 3.7:1; alternatively from 2.5:1 to 3.5:1; or alternatively from 2.9:1 to 3.1:1.

Oligomerization Process

The oligomerization catalyst system described herein may be utilized within an oligomerization process or a process to prepare an oligomerization product. Generally, the oligomerization process or process to prepare an oligomerization product comprises oligomerizing a feedstock olefin with the oligomerization catalyst as described herein.

In various embodiments and in accordance with one aspect, the feedstock olefin may comprise, consist essentially of, or consist of, an alpha olefin and the oligomerization process may be an oligomerization process for preparing an alpha olefin oligomerization product; alternatively, the feedstock olefin may comprise, consist essentially of, or consist of, a linear alpha olefin and the oligomerization process may be an oligomerization process for preparing an linear alpha olefin oligomerization product; or alternatively, the feedstock olefin may comprise, consist essentially of, consist of, a normal alpha olefin and the oligomerization process may be an oligomerization process for preparing a normal alpha olefin oligomerization product.

In one aspect, the oligomerization process for preparing an olefin oligomerization product may be an olefin trimerization process for preparing an olefin trimer product. In an embodiment, the trimerization feedstock olefin may comprise, consist essentially of, consist of, an alpha olefin and the oligomerization process can be an trimerization process for preparing an alpha olefin trimerization product; alternatively, the trimerization feedstock olefin may comprise, consist essentially of, or consist of, a linear alpha olefin and the oligomerization process may be an trimerization process for preparing an linear alpha olefin trimerization product; or alternatively, the trimerization feedstock olefin may comprise, consist essentially of, or consist of, a normal alpha olefin and the oligomerization process may be an trimerization process for preparing an normal alpha olefin trimerization product.

Generally, the feedstock olefin(s), alpha olefin(s), linear alpha olefin(s), or normal alpha olefin(s) may be $C_2$ to $C_{30}$, $C_2$ to $C_{16}$, or $C_2$ to $C_{10}$ olefin(s), alpha olefin(s), linear alpha olefin(s), or normal alpha olefin(s). In an embodiment, the olefin may comprise, consist essentially of, or consist of, ethylene. When the feedstock olefin comprises, consists essentially of, or consist of, ethylene, the oligomerization process may be an ethylene trimerization process, the trimer product may be 1-hexene, and the trimerization product comprises 1-hexene.

One composite catalyst system which may be used in the invention is the combination of chromium (III) ethylhexanoate, 2,5-diethylpyrrole, triethylaluminum, and diethylaluminum chloride. This composite catalyst system can be used, for example, to trimerize ethylene to form 1-hexene. Other catalyst applicable catalyst systems may be readily discerned from the present disclosure.

In one aspect, contacting and/or reacting the chromium compound, pyrrole compound, and metal alkyl is carried out in the presence of an unsaturated hydrocarbon. The unsaturated hydrocarbon can be any aromatic or aliphatic hydrocarbon, in a gas, liquid or solid state. In some embodiments, the unsaturated compound may be an aromatic hydrocarbon; alternatively, an unsaturated aliphatic compound. To effect thorough contacting of the chromium compound, the pyrrole compound, and metal alkyl, the unsaturated hydrocarbon may be in a liquid state. It will be understood, however, that some embodiments may be used in connection with appropriate catalyst systems, irrespective of the method of producing the catalyst system. In one aspect, the unsaturated hydrocarbon can be 1-hexene. Alternatively, the contacting and/or reacting the chromium compound, pyrrole compound, and metal alkyl can be carried out in the absence of 1-hexene.

The unsaturated hydrocarbon can have any number of carbon atoms per molecule. Usually, the unsaturated hydrocarbon will comprise less than 70 carbon atoms per molecule, or less than 20 carbon atoms per molecule. Exemplary unsaturated, aliphatic unsaturated hydrocarbon compounds include, but are not limited to, ethylene, 1-hexene, 1,3-butadiene, and mixtures thereof. In one aspect of the invention, the unsaturated aliphatic hydrocarbon compound is 1-hexene. If 1-hexene is the target oligomer to be formed, this may decrease the need for subsequent purification steps. Aromatic hydrocarbons that may be used as the unsaturated hydrocarbon in the preparation of the catalyst system may include, but are not limited to, $C_6$ to $C_{50}$ aromatic compounds; alternatively, $C_6$ to $C_{30}$ aromatic compounds; alternatively, $C_6$ to $C_{18}$ aromatic compounds; or alternatively, $C_6$ to $C_{10}$ aromatic compounds. Exemplary aromatic hydrocarbons include, but are not limited to, benzene, toluene, ethylbenzene, xylene, mesitylene, hexamethylbenzene, and mixtures thereof. In an embodiment, the aromatic compound may be toluene; alternatively ethylbenzene, or alternatively, xylene. Without being limited by theory, it is believed that that use of an unsaturated hydrocarbon during the preparation of the catalyst system improved catalyst system stability.

It should be recognized, that the reaction mixture comprising a chromium compound, the pyrrole compound, metal alkyl and unsaturated hydrocarbon can contain additional components which do not adversely affect and can enhance the resultant catalyst system, such as, for example, transitions metals and/or halides.

The amount of aromatic compound that may be used in the preparation of the oligomerization catalyst system may be in a range up to 15 weight percent, based on the amount of solvent in the reactor, range from 0.001 to 10 weight percent, or range from 0.01 to 5 weight percent. Excess aromatic compound may inhibit catalyst system activity and insufficient aromatic compound may not stabilize the catalyst system. Generally, the moles of aromatic compound per mole of metal in the transition metal compound (e.g. chromium compound) in the catalyst system may be in a range up to 6,000, range from 10 to 3,000, or range from 20 to 1,000 moles of aromatic compound per mole of metal (e.g. chromium compound) in the catalyst system.

Contacting of the aromatic compound and catalyst system may occur under any conditions sufficient to stabilize the catalyst system in the presence of heat. Generally, the temperatures for contacting may range from −50° C. to 70° C., range from −10° C. to 70° C., or range from 5° C. to 30° C. Generally, contacting times may be less than 5 hours, range from 0.01 seconds to 4 hours, or range from 0.1 seconds to 3 hours. Longer contact times may not improve catalyst system stability, and shorter contact times may be insufficient to allow complete contacting of the aromatic compound and catalyst system and, therefore, may not be sufficient to stabilize the catalyst system. Any pressure which allows thorough contacting of the aromatic compound and catalyst system may be used. Generally, any pressure which can maintain the aromatic compound and catalyst system in liquid form may be used. The catalyst system preparation is generally performed under an inert atmosphere, such as nitrogen or argon, to decrease the amount of water vapor and oxygen present. Nitrogen is often used due to cost and availability. In addition to the discussion herein, other applicable examples of transition metal compounds and oligomerization catalyst systems, and their exemplary preparation, are provided in U.S. Pat. No. 6,133,495 and U.S. Pat. No. 7,384,886, which are hereby incorporated by reference in their entireties for all purposes.

The oligomerization reaction products, e.g., olefin trimers, can be prepared from the catalyst system of this invention by solution, slurry, and/or gas phase reaction techniques using conventional equipment and contacting processes. Contacting of the monomer or monomers with a catalyst system can be effected by any manner known in the art. One convenient method is to suspend the catalyst system in an organic medium and to agitate the mixture to maintain the catalyst system in solution throughout the trimerization process. Other known contacting methods can also be employed.

For example, a continuous-feed autoclave reactor with a fluid jacket or internal heat transfer coil and any suitable stiffing mechanism, such as, for example, mechanical stirring or the sparging with an inert gas, typically nitrogen, may be used. In another embodiment, a loop reactor with mechanical stirring, such as, for example, a circulating pump, can be used. Alternatively, tubular reactions for carrying out the oligomerization may also be used in connection with the invention.

The oligomerization or trimerization process can be carried out in solvent which is used as the process medium. If employed, any number of hydrocarbon solvent may be used as the process medium for the oligomerization or trimerization reaction. In embodiment, the solvent that may be utilized as the process medium may be hydrocarbon or halogenated hydrocarbon; alternatively, a hydrocarbon; or alternatively a halogenated hydrocarbon. Hydrocarbons and halogenated hydrocarbon can include, for example, aliphatic hydrocarbons, aromatic hydrocarbons, petroleum distillates, halogenated aliphatic hydrocarbons, halogenated aromatic hydrocarbons, or combinations thereof; alternatively aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which may be useful as a solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons may be cyclic or acyclic and/or may be linear or branched, unless otherwise specified. Non-limiting examples of suitable acyclic aliphatic hydrocarbon solvents that may be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples of suitable cyclic aliphatic hydrocarbon solvents include cyclohexane, methyl cyclohexane; alternatively cyclohexane; or alternatively, methylcyclohexane. Aromatic hydrocarbons which may be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons that may be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene. Halogenated aliphatic hydrocarbons which may be useful as a solvent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons may be cyclic or acyclic and/or may be linear or branched, unless otherwise specified. Non-limiting examples of suitable halogenated aliphatic hydrocarbons which may be utilized include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which may be useful as a solvent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively chlorobenzene and dichlorobenzene.

The choice of the oligomerization solvent may be made on the basis of convenience in processing. For example, isobutane may be chosen to be compatible with diluents used for the formation of polyolefins in a subsequent processing step. In some embodiments, a reaction product or reaction feedstock olefin may be utilized as the solvent/process medium. For example, since 1-hexene may be the reaction product of an ethylene trimerization process, it may be chosen as the oligomerization solvent to decrease the need for separation.

In accordance with another embodiment of this invention, a slurry process can be carried out in a diluent (medium), which is a product of the olefin oligomerization process. Therefore, the choice of reactor diluent, or medium, may be based on the selection of the initial olefin reactant and/or the oligomerization product. For example, if the oligomerization catalyst is used to trimerize ethylene to 1-hexene, the solvent for the oligomerization reaction could be 1-hexene. If ethylene and hexene are trimerized, the oligomerization reaction solvent could be 1-hexene, and/or a trimerization product. If 1,3-butadiene was trimerized to 1,5-cyclooctadiene, the trimerization reactor solvent could be 1,3-butadiene or 1,5-cyclooctadiene.

Reaction temperatures and pressures can be any temperature and pressure which are suitable to trimerize the olefin reactants using the catalyst system. Generally, reaction temperatures are within a range of −20° C. to 250° C. In another aspect of the invention, reaction temperatures are within a range of 60° C. to 200° C. In yet another aspect, reaction temperatures are within a range of 80° C. to 150° C. Generally, reaction pressures are within a range of atmospheric to 2500 psig. In another aspect of the invention, reaction pressures may be within a range of atmospheric to 2500 psig; or alternatively, within a range of atmospheric to 1600 psig. In yet another aspect of the invention, the reaction pressure ranges between 300 psig and 900 psig. When the olefinic compound is ethylene, the reaction may be performed at an ethylene partial pressure ranging from 20 psi to 2500 psi; alternatively, from 100 psi to 2000; alternatively, from 200 psi to 1500 psi; or alternatively, from 300 psi to 1000 psi.

If the reaction temperature is too low can produce too much undesirable insoluble product, such as, for example, polymer, and if the reaction temperature is too high it can cause deactivation of the catalyst system and isomerization of the reaction products. A reaction pressure that is too low can result in low catalyst system activity.

Optionally, hydrogen may be added to the reactor to accelerate the reaction and/or increase catalyst system activity. If desired, hydrogen also may be added to the reactor to suppress polymer production. When hydrogen is utilized, the hydrogen partial pressure may range from 2 psi to 100 psi; alternatively, 5 psi to 75 psi; or alternatively, 10 psi to 50 psi.

The contents of the reactor may be agitated or stirred by an inert gas (e.g. nitrogen) purge, by introducing the reactant, hydrogen, fluid medium, or catalyst or exhausting the effluent in a manner causing agitation, by mechanical or magnetic stirring, or in any other suitable manner.

The reaction usually is run continuously by steadily charging lower 1-olefin reactant(s), catalyst system, and process medium and removing the liquid contents of the reactor. For example, a continuous stirred tank reactor system can be employed that includes feed systems for catalyst system, reactant and medium and a discharge system for the effluent. Alternatively, a batch process can also be employed.

The trimerization reaction is an exothermic process, so the reaction temperature usually can be regulated by circulating cooling water through a jacket or heat transfer coil, thus transferring heat out of the reactor. Efficient heat transfer out of the reactor enables effective maintenance of the desired reaction temperature. Another advantage of more effective heat transfer is that the trimerization reaction can be run at a higher throughput for a given temperature, which can improve production efficiency.

In an aspect, the reactor effluent is treated to deactivate the active catalyst system, and may further be treated to separate products, recycle the residual reactants, medium, and other components suitable for recycling, and dispose of any components that are not recycled.

When the oligomerization or trimerization process is deemed to be complete, the reactor effluent stream comprising solvent, olefin product(s), catalyst system, and some polymer and/or oligomer, may be contacted with an alcohol to deactivate the active catalyst system. Any alcohol which is soluble in the reactor effluent stream can be used. As used herein, the term "alcohol" includes monoalcohols, diols, and polyols. The alcohol may be selected by boiling point, molecular weight, or such that the alcohol will not azeotrope with the olefin monomer product. In some embodiments, the alcohol has a boiling point different from the olefin product in the reactor effluent stream. In an exemplary process, wherein the catalyst system is used to trimerize ethylene to 1-hexene, an alcohol with six or more carbon atoms per molecule may be used. In an embodiment the alcohol may be a $C_4$ to $C_{30}$, $C_4$ to $C_{20}$, or $C_4$ to $C_{12}$ alcohol. In some embodiments, the alcohol is selected to be easily removable from the oligomerization product (e.g. the trimerization product 1-hexene). Exemplary alcohols include, but are not limited to, 1-hexanol, 2-hexanol, 3-hexanol, 2-ethyl-hexanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, and mixtures thereof. In an embodiment the alcohol may be 2-ethyl-1-hexanol.

Alternatively, a low molecular weight diol or polyol, for example ethylene glycol, can be used as a catalyst deactivation agent. Diols and polyols commonly have much higher boiling points than monoalcohols of comparable molecular weight, and thus may be easily separated from some oligomerization products (e.g. the trimerization product 1-hexene).

The alcohol is added to the reactor effluent stream in an amount sufficient to quench and/or kill the catalyst system to inhibit, or halt: (1) production of undesirable solids, i.e., polymer; and/or (2) oligomerization (or alternatively, trimerization) product purity degradation due to isomerization, in the product separation process.

After the catalyst system has been deactivated, the oligomerization product(s), such as, for example, 1-hexene, can be removed. Any removal process can be used, including for example, distillation.

In an aspect, the oligomerization process or the process to prepare an oligomerization product comprising contacting the feedstock olefin with the oligomerization catalyst system using a pyrrole compound having substituent attached at the 2- and 5-positions and wherein at least one the carbon atoms of the groups attached to 2- and 5-position of the pyrrole ring is a secondary carbon atom (or alternatively, both of the carbon atoms of the groups attached to 2- and 5-position of the pyrrole ring is a secondary carbon atom) described herein produces less polymer than the process using an oligomerization catalyst system using 2,5-dimethylpyrrole as the pyrrole compound. In an aspect wherein the oligomerization is an ethylene trimerization process, the catalyst system using a pyrrole compound having substituent attached at the 2- and 5-positions and wherein at least one the carbon atoms of the groups attached to 2- and 5-position of the pyrrole ring is a secondary carbon atom (or alternatively, both of the carbon atoms of the groups attached to 2- and 5-position of the pyrrole ring is a secondary carbon atom) produces an oligomerization product having a greater selectivity to 1-hexene than an oligomerization catalyst system using 2,5-dimethylpyrrole as the pyrrole compound. In another aspect wherein the oligomerization is an ethylene trimerization process, the catalyst system using a pyrrole compound having substituent attached at the 2- and 5-positions and wherein at least one the carbon atoms of the groups attached to 2- and 5-position of the pyrrole ring is a secondary carbon atom (or alternatively, both of the carbon atoms of the groups attached to 2- and 5-position of the pyrrole ring is a secondary carbon atom) produces a 1-hexene product having a greater purity than an oligomerization catalyst system using 2,5-dimethylpyrrole as the pyrrole compound. In an embodiment, the catalyst system using a pyrrole compound having substituent attached at the 2- and 5-positions and wherein at least one the carbon atoms of the groups attached to 2- and 5-position of the pyrrole ring is a secondary carbon atom (or alternatively, both of the carbon atoms of the groups attached to 2- and 5-position of the pyrrole ring is a secondary carbon atom) produces an oligomerization selectivity to $C_6$ products at least 0.5%, 1.0%, 1.5%, or 2.0% (absolute) greater than the oligomerization selectivity to $C_6$ products produced by an oligomerization catalyst system using 2,5-dimethylpyrrole as the pyrrole compound.

In another aspect, an ethylene trimerization process or the process to prepare an ethylene trimerization product comprising contacting the feedstock olefin with the oligomerization catalyst system using a pyrrole compound having a hydrogen atom located on at least one pyrrole ring carbon atom adjacent to the nitrogen atom of the pyrrole ring and a bulky group located on a pyrrole ring carbon atom adjacent to any pyrrole carbon atom bearing the hydrogen atom adjacent to the nitrogen atom of the pyrrole ring (or alternatively, has a hydrogen atom located on each pyrrole ring carbon atom adjacent to the nitrogen atom of the pyrrole ring and a bulky group located on the pyrrole ring carbon atoms adjacent to the pyrrole ring carbon atom bearing the hydrogen atom adjacent to the nitrogen atom of the pyrrole ring) may have a higher productivity (g $C_6$/g transition metal—e.g. Cr) than the process using 2,4-dimethylpyrrole as the pyrrole compound, provides a higher selectivity to $C_6$ products than the process using 2,4-dimethylpyrrole as the pyrrole compound, and/or provides a higher purity 1-hexene product than the process using 2,4-dimethylpyrrole as the pyrrole compound; alternatively, has a higher productivity (g $C_6$/g transition metal—e.g. Cr) than the process using 2,4-dimethylpyrrole as the pyrrole compound; alternatively, provides a higher selectivity to $C_6$ products than the process using 2,4-dimethylpyrrole as the pyrrole compound; or alternatively, provides a higher purity 1-hexene product than the process using 2,4-dimethylpyrrole as the pyrrole compound. In an embodiment, the productivity (g $C_6$/g transition metal—e.g. Cr) of the catalyst system using any herein described pyrrole compound having a hydrogen atom located on at least one pyrrole ring carbon atom adjacent to the nitrogen atom of the pyrrole ring and a bulky group located on a pyrrole ring carbon atom adjacent to any pyrrole carbon atom bearing the hydrogen atom adjacent to the nitrogen atom of the pyrrole ring (or alternatively, has a hydrogen atom located on each pyrrole ring carbon atom adjacent to the nitrogen atom of the pyrrole ring and a bulky group located on the pyrrole ring carbon atoms adjacent to the pyrrole ring carbon atom bearing the hydrogen atom adjacent to the nitrogen atom of the pyrrole ring) may be 50%, 75%, or 100% (relative) greater than the productivity of the process using 2,4-dimethylpyrrole as the pyrrole compound. In some embodiments, the trimerization selectivity of a trimerization process utilizing the catalyst system using any herein described pyrrole compound having a hydrogen atom located on at least one pyrrole ring carbon atom adjacent to the nitrogen atom of the pyrrole ring and a bulky group located on a pyrrole ring carbon atom adjacent to any pyrrole carbon atom bearing the hydrogen atom adjacent to the nitrogen atom of the pyrrole ring (or alternatively, has a hydrogen atom located on each pyrrole ring carbon atom adjacent to the nitrogen atom of the pyrrole ring and a bulky group located on the pyrrole ring carbon atoms adjacent to the pyrrole ring carbon atom bearing the hydrogen atom adjacent to the nitrogen atom of the pyrrole ring) may be 1.0%, 1.5%, 2.0%, or 2.5% (absolute) greater than the oligomerization selectivity to $C_6$ products produced by an oligomerization catalyst system using 2,5-dimethylpyrrole as the pyrrole compound. In other embodiments, the purity of the 1-hexene produced by the trimerization process utilizing the catalyst system using any herein described pyrrole compound having a hydrogen atom located on at least one pyrrole ring carbon atom adjacent to the nitrogen atom of the pyrrole ring and a bulky group located on a pyrrole ring carbon atom adjacent to any pyrrole carbon atom bearing the hydrogen atom adjacent to the nitrogen atom of the pyrrole ring (or alternatively, has a hydrogen atom located on each pyrrole ring carbon atom adjacent to the nitrogen atom of the pyrrole ring and a bulky group located on the pyrrole ring carbon atoms adjacent to the pyrrole ring carbon atom bearing the hydrogen atom adjacent to the nitrogen atom of the pyrrole ring) may be 0.5%, 1.0%, 1.5%, or 2.0 (absolute) greater than the oligomerization purity of the 1-hexene product produced by an oligomerization catalyst system using 2,5-dimethylpyrrole as the pyrrole compound.

In yet another aspect, an ethylene trimerization process or the process to prepare an ethylene trimerization product comprising contacting the feedstock olefin with the oligomerization catalyst system using any herein described pyrrole compound having Formula P2, Formula P3, or Formula P4 wherein $R^{12p}$ and $R^{13p}$ of Formula P2 and $R^{22p}$ of Formula P3 may be any pyrrole substituent group disclosed herein while $R^{14p}$ of Formula P2, $R^{24p}$ of Formula P3, and $R^{33p}$ and $R^{34p}$ of Formula P4 may be any bulky pyrrole substituent disclosed herein may have a higher productivity (g $C_6$/g transition metal—e.g. Cr) than the process using 2,4-dimethylpyrrole as the pyrrole compound, provides a higher selectivity to $C_6$ products than the process using 2,4-dimethylpyrrole as the pyrrole compound, and/or provides a higher purity 1-hexene product than the process using 2,4-dimethylpyrrole as the pyrrole compound; alternatively, has a higher productivity (g $C_6$/g transition metal—e.g. Cr) than the process using 2,4-dimethylpyrrole as the pyrrole compound; alternatively, provides a higher selectivity to $C_6$ products than the process using 2,4-dimethylpyrrole as the pyrrole compound; or alternatively, provides a higher purity 1-hexene product than the process using 2,4-dimethylpyrrole as the pyrrole compound. In an embodiment, the productivity (g $C_6$/g transition metal—e.g. Cr) of the catalyst system utilizing the catalyst system using any herein described pyrrole compound having Formula P2, Formula P3, or Formula P4 wherein $R^{12p}$ and $R^{13p}$ of Formula P2 and $R^{22p}$ of Formula P3 may be any pyrrole substituent group disclosed herein while $R^{14p}$ of Formula P2, $R^{24p}$ of Formula P3, and $R^{33p}$ and $R^{34p}$ of Formula P4 may be any herein described bulky pyrrole substituent may be 50%, 75%, or 100% (relative) greater than the productivity of the process using 2,4-dimethylpyrrole as the pyrrole compound. In some embodiments, the trimerization selectivity of a trimerization process utilizing the catalyst system using any herein described pyrrole compound having Formula P2, Formula P3, or Formula P4 wherein $R^{12p}$ and $R^{13p}$ of Formula P2 and $R^{22p}$ of Formula P3 may be any pyrrole substituent group disclosed herein while $R^{14p}$ of Formula P2, $R^{24p}$ of Formula P3, and $R^{33p}$ and $R^{34p}$ of Formula P4 may be any herein described bulky pyrrole substituent may be 1.0%, 1.5%, 2.0%, or 2.5% (absolute) greater than the oligomerization selectivity to $C_6$ products produced by an oligomerization catalyst system using 2,5-dimethylpyrrole as the pyrrole compound. In other embodiments, the purity of the 1-hexene produced by the trimerization process utilizing the catalyst system using any herein described pyrrole compound having Formula P2, Formula P3, or Formula P4 wherein $R^{12p}$ and $R^{13p}$ of Formula P2 and $R^{22p}$ of Formula P3 may be any pyrrole substituent group disclosed herein while $R^{14p}$ of Formula P2, $R^{24p}$ of Formula P3, and $R^{33p}$ and $R^{34p}$ of Formula P4 may be any herein described bulky pyrrole substituent may be 0.5%, 1.0%, 1.5%, or 2.0 (absolute) greater than the oligomerization purity of the 1-hexene product produced by an oligomerization catalyst system using 2,5-dimethylpyrrole as the pyrrole compound.

Articles Prepared in Accordance with this Disclosure

According to yet a further aspect of this disclosure and in the various embodiments, this disclosure encompasses various articles prepared from the olefin oligomers made by the disclosed process. For example and not as a limitation, this disclosure encompasses an article prepared from the oligomerization product produced from the process as described herein. For example, the article can be produced using the oligomerization product in which the oligomerization product is a copolymer. Also by way of example, the article can be produced using the oligomerization product in which the oligomerization product is a polyethylene copolymer and the oligomerization product is 1-hexene.

In a further aspect, and also by way of example, the article can be produced using the oligomerization product in which the oligomerization product is a high density polyethylene, a low density polyethylene, a medium density polyethylene, a linear low density polyethylene. In these aspects, the oligomerization product can be subjecting to blending, heating, melting, compounding, extruding, injection molding, precision molding, blow molding, forming a film, forming a coating, or any combination thereof, in forming the article.

Comparative Results

Figure 2:
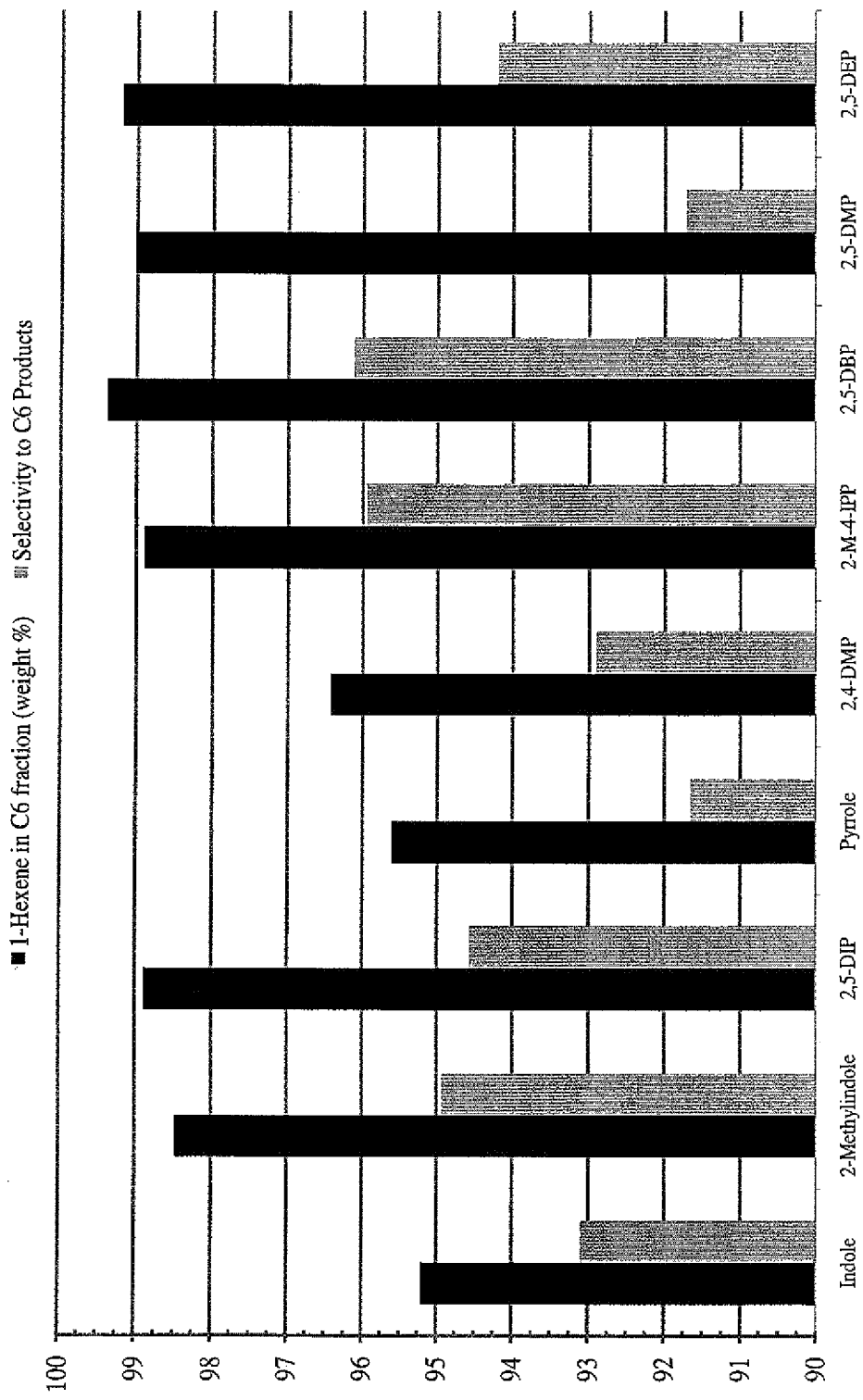
FIG. 2 is a bar chart of the $C_6$ selectivity and 1-hexene purity for chromium-based catalyst systems containing certain pyrrole compounds.

Referring to FIGS. 1 and 2 and Tables 1 and 2, the oligomerization studies were carried out to compare the catalytic behavior of different pyrroles under standard selective 1-hexene oligomerization reaction conditions to identify pyrrole compounds that provide active ethylene trimerization catalyst systems, determine their relative levels of oligomerization activity, determine the catalyst system's productivity, determine the catalyst system's selectivity to $C_6$ products, and/or determine the purity of the $C_6$ fraction (i.e. the weight % of 1-hexene found in the $C_6$ products produced in the oligomerization.

FIG. 1 illustrates a plot of the $C_6$ productivities (g C6/g Cr) as a function of temperature (° C.), for chromium-based catalyst systems prepared using the following pyrroles: 2,5-dimethylpyrrole (2,5-DMP); 2,5-dibenzylpyrrole (2,5-DBP); 2,4-dimethylpyrrole (2,4-DMP); 2-methyl-4-isopropypyrrole (2-M-4-IPP; and 2,5-diethylpyrrole (2,5-DEP) over the tested temperatures. As can be seen in FIG. 1, each pyrrole has a unique temperature profile in the oligomerization catalyst system and can optimized optimum or desirable operating conditions for the catalyst system using a particular pyrrole compound. From FIG. 1, it can be seen that the productivity of the catalyst systems using 2,5-disubstituted pyrrole and 2,4-disubstituted having a bulky substituent in the 4-position on the pyrrole ring were more acutely affected by variations in temperature than other catalyst systems. The data illustrated in FIG. 1 are provided in detail in Table 1.

Table 2 data provide the 1-hexene purity (% 1-hexene of $C_6$ product produced in the oligomerization), shown as in FIG. 2, and the $C_6$ selectivity, shown as in FIG. 2, for the indicate pyrrole compounds. These data are reported at the temperature (° C.) of the highest observed productivity (g C6/g Cr), which is provided in Table 2, using the catalyst prepared according to the Examples. Among other things, these data illustrate that 2,5-disubstituted pyrroles provide catalyst systems with higher productivity that those that contain non-2, 5-disubstituted pyrroles. Additionally, these data show that 2,4-substitued pyrroles having a bulky substituent in the 4-position of the pyrrole ring provide catalyst systems that have increased $C_6$ productivities, increased $C_6$ selectivities, and/or produce a $C_6$ product having a higher 1-hexene purity than catalyst system using a 2,4-substitued pyrrole that does not have a bulky substituent in the 4-position of the pyrrole ring (e.g. 2,4-dimethyl pyrrole. Generally, the catalytic productivity was observed to increase on moving from the non-substituted pyrrole, to the 2,4-disubstitued pyrrole, to 2- or 5-substituted pyrrole, to the prototypical 2,5-dimethylpyrrole.

The FIG. 2 and Table 2 data further illustrates the highest 1-hexene purities and C6 selectivities generally are obtained with the 2,5-disubstituted pyrrole compound or 2,4-disubstituted compounds having a bulky substituent in the 4-position of the pyrrole ring have at their highest measured catalyst productivity temperatures. As indicated in FIG. 2, the 2,5-DMP, 2,5-DEP, 2,5-DIP, 2,5-DBP, 2-M-4-IPP, as well as others such as 2-MeInd, would appear to offer a good combination of selectivity and purity.

In other comparisons, 2-methyl-3-ethyl-5-methylpyrrole (productivity ~21,700 g C6/g Cr) and 2-methylindole (productivity ~3,500 g C6/g Cr)—two compounds characterized by a similar substitution pattern and similar steric congestion—provide very different productivities. While not intending to be bound by theory, it is possible that the electron-withdrawing phenyl group fused to the pyrrole ring in 2-methyl indole produces a catalyst with low activity. As a further illustration, indole (productivity ~800 g C6/g Cr), which also has an electron-withdrawing group fused to the pyrrole ring, produces a catalyst with almost an order of magnitude lower productivity than the pyrrole catalyst (productivity ~6,400 g C6/g Cr). Again, while not intending to be theory-bound, it is possible that electronic effects may reduce the productivity of 2,5-dibenzylpyrrole (productivity ~23, 400 g C6/g Cr) as compared to that of 2,5-diethylpyrrole (productivity ~75,800 g C6/g Cr), although increased steric effects may play a significant role.

General Disclosure Information

All publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a $C_1$ to $C_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, Applicants intend to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a $C_1$ to $C_{10}$ alkyl group is intended to literally encompass a $C_1$ to $C_6$ alkyl, a $C_4$ to $C_8$ alkyl, a $C_2$ to $C_7$ alkyl, a combination of a $C_1$ to $C_3$ and a $C_5$ to $C_7$ alkyl, and so forth. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that may be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

For any particular compound disclosed herein, the general structure or name presented is also intended to encompass all structural isomers, conformational isomers, and stereoisomers that may arise from a particular set of substituents, unless indicated otherwise. Thus, a general reference to a compound includes all structural isomers unless explicitly indicated otherwise; e.g. a general reference to butane include n-pentane, 2-methyl-butane, and 2,2-dimethylpropane. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that may arise from a particular set of substituents.

The present disclosure is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may be suggested to one of ordinary skill in the art without departing from the spirit of the present invention or the scope of the appended claims.

In the following examples, unless otherwise specified, the syntheses and preparations described therein were carried out under an inert atmosphere such as nitrogen and/or argon. Solvents were purchased from commercial sources and were typically dried prior to use. Unless otherwise specified, reagents were obtained from commercial sources.

EXAMPLES

General Experimental Procedures and Starting Materials

Unless specified otherwise, all reactions were performed under an inert atmosphere. All glassware was dried in an oven at 100° C. for 4 hours and brought into an inert atmosphere glove box (dry box) while warm. All solvents were purchased from Aldrich as anhydrous grade and were stored over freshly activated 5 Å molecular sieves.

A. Pyrroles.

The following abbreviations are used for the pyrrole and indole ligands used herein: 2,4-dimethylpyrrole (2,4-DMP); 2-methyl-4-isopropylpyrrole (2-M-4-IPP); 2,5-dimethylpyrrole (2,5-DMP or DMP); 2,5-diethylpyrrole (2,5-DEP or DEP); 2,5-dibenzylpyrrole (2,5-DBP or DBP); 2,5-diisopropylpyrrole (2,5-DIP or DIP); indole (Ind); 2-methylindole (2-MeInd); and pyrrole (Pyr).

The pyrrole compounds 2,4-dimethylpyrrole (2,4-DMP), indole, and 2-methylindole were purchased from Aldrich. Both indole (RP>99%) and 2-methylindole (RP 98%) were dried under vacuum at 110° C. for several hours without further purification (RP is the reported purity in wt %; MP is the measured purity in wt %). The 2,4-dimethylpyrrole (2,4-DMP, RP 97%) was purified by distillation under nitrogen (bp=165-167° C.) producing a colorless liquid (MP 99.5%).

Other pyrrole ligands, such as 2,5-diethylpyrrole (2,5-DEP), 2,5-dibenzylpyrrole (2,5-DBP), 2,5-diisopropylpyrrole (2,5-DIP), and 2-methyl-4-isopropypyrrole (2-M-4-IPP) were obtained from Chemstep (Carbon-Blanc, France). The 2,5-DIP(RP>95%) was received as a colorless liquid (MP 96.8%) and was used without further purification. 2,5-DEP (RP>97%) was distilled (MP 98.5%) prior to use. The 2,5-DBP (RP 82%) was received as an orange waxy material (MP 82.2%) and was used without further purification. 2-M-4-IPP was distilled (MP 98.1%) prior to use. The identity of these four pyrroles was confirmed by GC-MS.

B. Catalyst Preparation.

A catalyst solution was prepared using the standard procedure described here, in which the molar ratios of TEA (triethylaluminum) to DEAC (diethylaluminum chloride) to pyrrole compound to Cr were standardized to TEA:DEAC:pyrrole:Cr=11:8:3:1. Anhydrous, degassed ethylbenzene was added to a dry vial in a drybox. To this vial was added neat triethylaluminum (TEA) and neat diethylaluminum chloride (DEAC). The contents were mixed and allowed to stand for 15 minutes. The selected pyrrole was then slowly added, as gas evolution was observed in most cases. Chromium(III) 2-ethylhexanoate (7.25 wt % Cr in ethylbenzene) was used as the transition metal compound and was added slowly to the alkylaluminum/pyrrole solution with stirring. The catalyst solution was diluted to a concentration of 5.6 mg Cr/mL by adding an appropriate amount of ethylbenzene to constitute the active catalyst what was used as prepared. Orange colored solutions were observed for 2,4-DMP, 2-methylindole, and 2,5-DEP based catalyst, which are typical. 2,5-DBP initially produced an orange solution, but gradually precipitated a noticeable amount of grey solid over the course of 24 h. Both indole and pyrrole produced an orange solution with a white, fluffy solid which was removed by filtration. 2,5-DIP produced copious amounts of black precipitate suggesting that the catalyst solution was fairly unstable

Example 1

Oligomerization Reactions

Oligomerization reaction studies comparing the catalytic behavior of different pyrroles under standard selective 1-hexene oligomerization reaction conditions, were performed as follows. The standard reactor was a 1 L batch reactor, and oligomerization reactions were carried out at the indicated temperature under 50 psig $H_2$, and under 850 psig ethylene with ethylene uptake on demand, over a 30 minute run time, using 2.5 mg Cr, in 450 mL of cyclohexane. This methodology was useful for identifying various substituted pyrroles that provided reactive catalysts.

Catalyst System Productivity as a Function of Temperature

The activity of selected pyrroles and their catalyst systems was investigated. Particularly, catalyst systems that employed 2,5-dimethylpyrrole (2,5-DMP), 2,5-dibenzylpyrrole (2,5-DBP), 2,4-dimethylpyrrole (2,4-DMP), pyrrole, 2,5-diethylpyrrole (2,5-DEP), and 2-methyl-4-isopropylpyrrole (2-M-4-IPP) were investigated for their catalytic temperature profile, in which their activity and productivity were examined as a function of temperature. FIG. 1 illustrates a plot of productivity (g $C_6$/g Cr) as a function of temperature (° C.), for chromium-based catalyst systems prepared using the following pyrroles: 2,5-dimethylpyrrole (2,5-DMP); 2,5-dibenzylpyrrole (2,5-DBP); 2,4-dimethylpyrrole (2,4-DMP); pyrrole; 2,5-diethylpyrrole (2,5-DEP), and 2-methyl-4-isopropylpyrrole (2-M-4-IPP). The FIG. 1 productivity versus temperature data are listed in Table 1. Among other things, these studies indicated that each pyrrole typically is characterized by its own unique temperature profile, which can be readily ascertained, and which can be used to establish optimum or desirable operating conditions.

As illustrated in FIG. 1 and the data in Table 1, one consequence of comparing the productivities of various catalyst systems at a single standard temperature is that an incomplete comparative picture may result. For example, at higher temperatures (130-135° C.) the 2,5-DMP and 2,5-DEP catalyst systems provide somewhat comparable results (25,900 g C6/g Cr and 22,828 g C6/g Cr, respectively), but when compared at their respective highest productivities at about 92-95° C., this difference in productivity was exaggerated. At these lower temperatures, the 2,5-DMP (99,460 g C6/g Cr, 95° C.) is about 31% more productive than the corresponding 2,5-DEP catalyst system (75,757 g C6/g Cr, 92° C.).

Catalyst System Productivity as a Function of Pyrrole Substitution

The data the oligomerizations, data provided in Table 1 and FIG. 1, illustrate that 2,5-disubstituted pyrroles provide catalysts with generally higher productivity that those that contain non-2,5-disubstituted pyrroles. Generally, the catalytic productivity was observed to increase on moving from the non-substituted pyrrole to 2,4-dimethylpyrrole, to 2,4-disubstituted pyrroles having a bulky substituent in the 4-position, to the 2,5-disubstituted pyrroles (2,5-dimethylpyrrole being the prototypical 2,5-disubstituted pyrrole).

TABLE 1

Productivity (g $C_6$/g Cr) versus temperature for a variety of pyrrole compounds. These data are illustrated in FIG. 1.

| Pyrrole Compound | Temperature (° C.) | Productivity (g C6/g Cr) |
|---|---|---|
| DEP | 92 | 75,757 |
|  | 98 | 74,478 |
|  | 105 | 66,443 |
|  | 115 | 39,233 |
|  | 130 | 22,828 |
| 2,5-DMP | 95 | 99,460 |
|  | 105 | 87,300 |
|  | 115 | 60,660 |
|  | 125 | 43,000 |
|  | 135 | 25,900 |
| DBP | 45 | 2,792 |
|  | 70 | 15,021 |
|  | 85 | 23,411 |
|  | 115 | 9,325 |
| 2,4-DMP | 100 | 11,882 |
|  | 115 | 14,278 |
|  | 130 | 13,523 |
|  | 145 | 13,404 |
| 2-methy4-isopropyl pyrrole | 100 | 30,300 |
|  | 115 | 43,900 |
| pyrrole | 90 | 6,427 |
|  | 115 | 6,138 |
|  | 125 | 2,977 |

1-Hexene Purity and Selectivity as a Function of Pyrrole Substitution

Table 2 and FIG. 2 provide a comparison of the $C_6$ selectivities (% $C_6$ of total oligomerized product) and % 1-hexene (by weight) in the $C_6$ product (1-hexene purity) for catalyst systems using the indicated pyrroles at the catalyst system's highest observed productivity. FIG. 2 and Table 2 data illustrate the highest 1-hexene purities and $C_6$ selectivities generally are obtained with the 2,5-disubstituted pyrrole compounds and 2,4-disubstituted pyrroles having a bulky substituent in the 4-position at their highest measured catalyst productivity temperatures. As indicated in FIG. 2, the 2,5-DMP, 2,5-DEP, 2,5-DIP, and 2,5-DBP, 2-M-4-IPP, as well as others such as 2-MeInd, would appear to offer a good combination of $C_6$ selectivity and 1-hexene purity.

1-Hexene Productivity as a Function of Pyrrole-Based or Indole-Based Catalyst Systems Additional experiments were conducted to evaluate the potential effect of using fused-ring compounds such as indole or substituted indole as the nitrogen-containing compound in the catalysts systems. 2-Methyl-3-ethyl-5-methylpyrrole (21,700 g $C_6$/g Cr) and 2-methylindole (3,500 g $C_6$/g Cr) have a similar substitution pattern, with similar steric congestion. However, the productivities of the catalyst systems produced using these tow compound differed by over 600%. Moreover, indole (800 g $C_6$/g Cr) produced a catalyst with almost an order of magnitude lower productivity than the pyrrole catalyst (6,400 g $C_6$/g Cr). These data can be compared to the productivity of 2,5-dibenzylpyrrole (23,400 g $C_6$/g Cr) as compared to that of 2,5-diethylpyrrole (75,800 g $C_6$/g Cr), although increased steric effects may play a role in this observed productivity.

TABLE 2

1-Hexene purity (% of total $C_6$ product) and $C_6$ selectivity (% of total oligomerized product) for a variety of pyrrole compounds, reported at the temperature (° C.) of the highest observed productivity (g $C_6$/g Cr), using the catalyst prepared according to the Examples.

| Pyrrole Compound | Productivity (g $C_6$/g Cr) | Temperature (° C.) | 1-Hexene Purity | $C_6$ Selectivity |
|---|---|---|---|---|
| 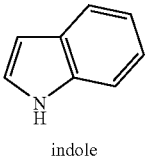 indole | 789 | 115 | 95.21 | 93.1 |
| 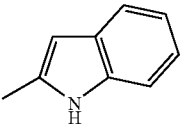 2-methylindole | 3,508 | 115 | 98.48 | 94.93 |
| 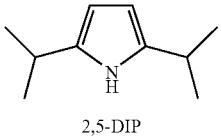 2,5-DIP | 3,631 | 115 | 98.89 | 94.57 |
|  pyrrole | 6,427 | 90 | 96.54 | 95.39 |
| 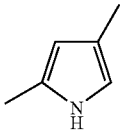 2,4-DMP | 14,284 | 115 | 96.46 | 92.89 |
| 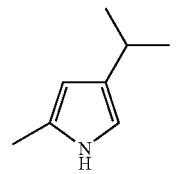 2-methy4-isopropyl pyrrole | 43,900 | 100 | 98.90 | 95.95 |
| 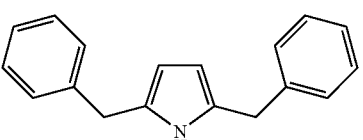 DBP | 23,411 | 85 | 99.38 | 96.13 |
| 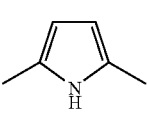 2,5-DMP | 99,456 | 95 | 99.02 | 91.72 |

TABLE 2-continued

1-Hexene purity (% of total $C_6$ product) and $C_6$ selectivity (% of total oligomerized product) for a variety of pyrrole compounds, reported at the temperature (° C.) of the highest observed productivity (g $C_6$/g Cr), using the catalyst prepared according to the Examples.

| Pyrrole Compound | Productivity (g $C_6$/g Cr) | Temperature (° C.) | 1-Hexene Purity | $C_6$ Selectivity |
|---|---|---|---|---|
| 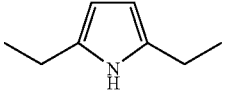 DEP | 75,757 | 92 | 99.20 | 94.21 |

What is claimed is:

1. A catalyst system comprising:
   a) a transition metal compound;
   b) a pyrrole compound having Formula P2, P3, or P4:

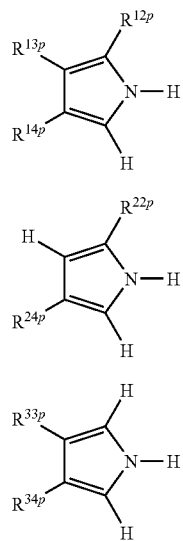

wherein
   i) $R^{12p}$ and $R^{13p}$ of Formula P2 and $R^{22p}$ of Formula P3 independently are a $C_1$ to $C_{15}$ hydrocarbyl group; and
   ii) $R^{14p}$ in Formula P2, $R^{24p}$ in Formula P3, and $R^{33p}$ and $R^{34p}$ in Formula P4 independently are a bulky $C_3$ to $C_{15}$ hydrocarbyl group or a bulky $C_3$ to $C_{45}$ silyl group; and
   c) a metal alkyl.

2. The catalyst system of claim 1, wherein
   a) the transition metal compound comprises a chromium compound; and
   b) the metal alkyl comprises an alkylaluminum compound.

3. The catalyst system of claim 2, wherein the $R^{14p}$ group in Formula P2, $R^{24p}$ group in Formula P3, and $R^{33p}$ and $R^{34p}$ group in Formula P4 are attached such that
   i) the carbon atom attached to the pyrrole ring is attached to three or four carbon atoms,
   ii) the carbon atom adjacent to the carbon atom attached to pyrrole ring is attached to three or four carbon atoms, or
   iii) the $C_3$ to $C_{45}$ silyl group has Formula Si1

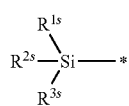

wherein $R^{1s}$, $R^{2s}$, and $R^{3s}$ independently are a $C_1$ to $C_{15}$ hydrocarbyl group.

4. The catalyst system according to claim 2, wherein $R^{14p}$ in Formula P2, $R^{24p}$ in Formula P3, and $R^{33p}$ and $R^{34p}$ in Formula P4 independently are a propan-2-yl group, a butan-2-yl, a 2-methylpropan-1-yl group, a 2-methylpropan-2-yl group, a pentan-2-yl group, a pentan-3-yl group, a 2-methylbutan-1-yl group, a 2-methylbutan-2-yl group, a 3-methylbutan-2-yl group, 2,2-dimethylpropan-1-yl group, a hexan-2-yl group, a hexan-3-yl group, a 2-methylpentan-1-yl group, 2-ethylbutan-1-yl group, a 2-methylpentan-2-yl group, a 2,3-dimethylbutan-1-yl group, a 2,3-dimethylbutan-2-yl group, a heptan-2-yl group, a heptan-3-yl group, a heptan-4-yl group, a 2-methylhexan-1-yl group, a 2-ethylpentan-1-yl group, a 2-methylhexan-2-yl group, a 2,3-dimethylpentan-1-yl group, a 2,3-dimethylpentan-2-yl group, a 2,3,3-trimethylpentan-1-yl group, a 2,3,3-trimethylpentan-2-yl group, an octan-2-yl group, an octan-3-yl group, an octan-4-yl group, a 2-methylheptan-1-yl group, a 2-ethylhexan-1-yl group, a 2-methylheptan-2-yl group, a nonan-2-yl group, a nonan-3-yl group, a nonan-4-yl group, a nonan-5-yl group, a decan-2-yl group, a decan-3-yl group, a decan-4-yl group, or a decan-5-yl group.

5. The catalyst system according to claim 2, wherein the pyrrole compound is 2-methyl-4-isopropylpyrrole, 2-ethyl-4-isopropylpyrrole, 2-methyl-4-t-butylpyrrole, or 2-ethyl-4-t-butylpyrrole.

6. The catalyst system according to claim 2, wherein the chromium compound comprises a chromium(II) or chromium(III) halide, 1,3-diketonate, or carboxylate.

7. The catalyst system according to claim 2, wherein the chromium compound comprises a chromium(II) or chromium(III) carboxylate wherein each carboxylate is a $C_4$ to $C_{19}$ carboxylate.

8. The catalyst system according to claim 2, wherein the chromium compound is chromium(III) 2-ethylhexanoate, chromium(III) octanoate, chromium(III) 2,2,6,6,-tetramethylheptanedionate, chromium(III) naphthenate, chromium(III) acetate, chromium(III) propionate, chromium(III) butyrate, chromium(III) neopentanoate, chromium(III) laurate, chromium(III) stearate, chromium(III) oxalate, chromium(II) bis(2-ethylhexanoate), chromium(II) acetate, chromium(II) propionate, chromium(II) butyrate, chromium(II) neopentanoate, chromium(II) laurate, chromium(II) stearate, chromium(II) oxalate, or any combination thereof.

9. The catalyst system according to claim 2, wherein the transition metal compound comprises a chromium(II) or chromium(III) carboxylate wherein each carboxylate is a $C_4$ to $C_{19}$ carboxylate and the metal alkyl comprises a mixture of triethylaluminum and diethylaluminum chloride.

10. The catalyst system according to claim 1, wherein the metal alkyl comprises a group 1, 2, 11, 12, 13, or 14 of the Periodic Table metal alkyl compound.

11. The catalyst system according to claim 1, further comprising a halogen containing compound selected from a metal halide, an alkyl metal halide, or an organic halide.

12. The catalyst system of claim 1, wherein:
a) the transition metal compound is chromium(III) 2-ethylhexanoate, chromium(III) octanoate, chromium(III) 2,2,6,6,-tetramethylheptanedionate, chromium(III) naphthenate, chromium(III) acetate, chromium(III) propionate, chromium(III) butyrate, chromium(III) neopentanoate, chromium(III) laurate, chromium(III) stearate, chromium(III) oxalate, chromium(II) bis(2-ethylhexanoate), chromium(II) acetate, chromium(II) propionate, chromium(II) butyrate, chromium(II) neopentanoate, chromium(II) laurate, chromium(II) stearate, chromium(II) oxalate, or a combination thereof;
b) the pyrrole compound is 2-methyl-4-isopropylpyrrole, 2-ethyl-4-isopropylpyrrole, 2-methyl-4-t-butylpyrrole, 2-ethyl-4-t-butylpyrrole, or a combination thereof; and
c) the metal alkyl is a trialkylaluminum compound, an alkylaluminum halide compound, or a combination thereof.

13. An oligomerization process comprising:
a) contacting a feedstock olefin with the catalyst system of claim 1; and
b) oligomerizing the olefin under oligomerization conditions to form an oligomerization product.

14. The oligomerization process of claim 13, wherein
a) the feedstock olefin comprises ethylene and the oligomerization product comprises 1-hexene,
b) the transition metal compound comprises a chromium (II) or chromium(III) carboxylate wherein each carboxylate is a $C_4$ to $C_{19}$ carboxylate; and
c) the metal alkyl comprises a mixture of triethylaluminum and diethylaluminum chloride.

15. The oligomerization process of claim 14, wherein the process provides a higher selectivity to $C_6$ products than a process using 2,4-dimethylpyrrole as the pyrrole compound.

16. The oligomerization process of claim 14, wherein the process provides a higher purity 1-hexene product than a process using 2,4-dimethylpyrrole as the pyrrole compound.

17. The oligomerization process of claim 13, wherein the pyrrole compound is 2-methyl-4-isopropylpyrrole, 2-ethyl-4-isopropylpyrrole, 2-methyl-4-t-butylpyrrole, or 2-ethyl-4-t-butylpyrrole.

18. The oligomerization process of claim 14, wherein the $R^{14p}$ group in Formula P2, $R^{24p}$ group in Formula P3, and $R^{33p}$ and $R^{34p}$ group in Formula P4 are attached such that
i) the carbon atom attached to the pyrrole ring is attached to three or four carbon atoms,
ii) the carbon atom adjacent to the carbon atom attached to pyrrole ring is attached to three or four carbon atoms, or
iii) the $C_3$ to $C_{45}$ silyl group has Formula Si1

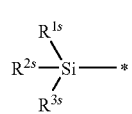

wherein $R^{1s}$, $R^{2s}$, and $R^{3s}$ independently are a $C_1$ to $C_{15}$ hydrocarbyl group.

19. The oligomerization process of claim 14, wherein $R^{14p}$ in Formula P2, $R^{24p}$ in Formula P3, and $R^{33p}$ and $R^{34p}$ in Formula P4 independently are a propan-2-yl group, a butan-2-yl, a 2-methylpropan-1-yl group, a 2-methylpropan-2-yl group, a pentan-2-yl group, a pentan-3-yl group, a 2-methylbutan-1-yl group, a 2-methylbutan-2-yl group, a 3-methylbutan-2-yl group, 2,2-dimethylpropan-1-yl group, a hexan-2-yl group, a hexan-3-yl group, a 2-methylpentan-1-yl group, 2-ethylbutan-1-yl group, a 2-methylpentan-2-yl group, a 2,3-dimethylbutan-1-yl group, a 2,3-dimethylbutan-2-yl group, a heptan-2-yl group, a heptan-3-yl group, a heptan-4-yl group, a 2-methylhexan-1-yl group, a 2-ethylpentan-1-yl group, a 2-methylhexan-2-yl group, a 2,3-dimethylpentan-1-yl group, a 2,3-dimethylpentan-2-yl group, a 2,3,3-trimethylpentan-1-yl group, a 2,3,3-trimethylpentan-2-yl group, an octan-2-yl group, an octan-3-yl group, an octan-4-yl group, a 2-methylheptan-1-yl group, a 2-ethylhexan-1-yl group, a 2-methylheptan-2-yl group, a nonan-2-yl group, a nonan-3-yl group, a nonan-4-yl group, a nonan-5-yl group, a decan-2-yl group, a decan-3-yl group, a decan-4-yl group, or a decan-5-yl group.

20. The oligomerization process of claim 13, wherein:
a) the transition metal compound is chromium(III) 2-ethylhexanoate, chromium(III) octanoate, chromium(III) 2,2,6,6,-tetramethylheptanedionate, chromium(III) naphthenate, chromium(III) acetate, chromium(III) propionate, chromium(III) butyrate, chromium(III) neopentanoate, chromium(III) laurate, chromium(III) stearate, chromium(III) oxalate, chromium(II) bis(2-ethylhexanoate), chromium(II) acetate, chromium(II) propionate, chromium(II) butyrate, chromium(II) neopentanoate, chromium(II) laurate, chromium(II) stearate, chromium(II) oxalate, or a combination thereof;
b) the pyrrole compound is 2-methyl-4-isopropylpyrrole, 2-ethyl-4-isopropylpyrrole, 2-methyl-4-t-butylpyrrole, 2-ethyl-4-t-butylpyrrole, or a combination thereof; and
c) the metal alkyl is a trialkylaluminum compound, an alkylaluminum halide compound, or a combination thereof.

21. A process for preparing a catalyst system, comprising contacting:
a) a transition metal compound;
b) a pyrrole compound having Formula P2, P3, or P4:

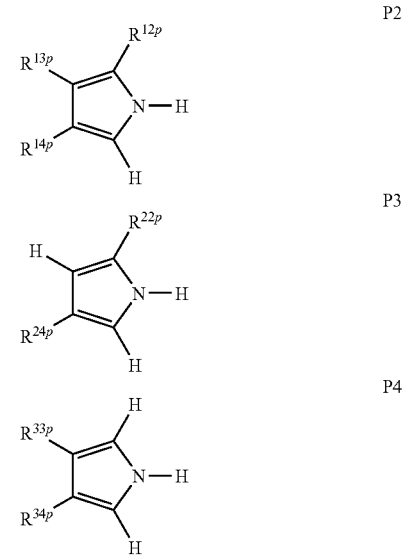

wherein
i) $R^{12p}$ and $R^{13p}$ of Formula P2 and $R^{22p}$ of Formula P3 independently are a $C_1$ to $C_{15}$ hydrocarbyl group; and
ii) $R^{14p}$ in Formula P2, $R^{24p}$ in Formula P3, and $R^{33p}$ and $R^{34p}$ in Formula P4 independently are a bulky $C_3$ to $C_{15}$ hydrocarbyl group or a bulky $C_3$ to $C_{45}$ silyl group; and
c) a metal alkyl.

22. The process of claim 21, wherein
a) the transition metal compound comprises a chromium (II) or chromium(III) carboxylate wherein each carboxylate is a $C_4$ to $C_{19}$ carboxylate; and
b) the metal alkyl comprises a mixture of triethylaluminum and diethylaluminum chloride.

23. The process of claim 22, wherein the transition metal compound, the pyrrole compound, and the metal alkyl are contacted in the presence of an unsaturated compound to stabilize the catalyst system, wherein the unsaturated compound comprises a $C_6$ to $C_{18}$ aromatic compound.

24. The process of claim 23, wherein the aromatic compound comprises benzene, toluene, ethylbenzene, xylene, mesitylene, hexamethylbenzene, or mixtures thereof.

25. The process of claim 22, wherein $R^{14p}$ in Formula P2, $R^{24p}$ in Formula P3, and $R^{33p}$ and $R^{34p}$ in Formula P4 independently are a propan-2-yl group, a butan-2-yl, a 2-methylpropan-1-yl group, a 2-methylpropan-2-yl group, a pentan-2-yl group, a pentan-3-yl group, a 2-methylbutan-1-yl group, a 2-methylbutan-2-yl group, a 3-methylbutan-2-yl group, 2,2-dimethylpropan-1-yl group, a hexan-2-yl group, a hexan-3-yl group, a 2-methylpentan-1-yl group, 2-ethylbutan-1-yl group, a 2-methylpentan-2-yl group, a 2,3-dimethylbutan-1-yl group, a 2,3-dimethylbutan-2-yl group, a heptan-2-yl group, a heptan-3-yl group, a heptan-4-yl group, a 2-methylhexan-1-yl group, a 2-ethylpentan-1-yl group, a 2-methylhexan-2-yl group, a 2,3-dimethylpentan-1-yl group, a 2,3-dimethylpentan-2-yl group, a 2,3,3-trimethylpentan-1-yl group, a 2,3,3-trimethylpentan-2-yl group, an octan-2-yl group, an octan-3-yl group, an octan-4-yl group, a 2-methylheptan-1-yl group, a 2-ethylhexan-1-yl group, a 2-methylheptan-2-yl group, a nonan-2-yl group, a nonan-3-yl group, a nonan-4-yl group, a nonan-5-yl group, a decan-2-yl group, a decan-3-yl group, a decan-4-yl group, or a decan-5-yl group.

26. The process of claim 22, wherein the pyrrole compound is 2-methyl-4-isopropylpyrrole, 2-ethyl-4-isopropylpyrrole, 2-methyl-4-t-butylpyrrole, or 2-ethyl-4-t-butylpyrrole.

27. The process of claim 22, wherein the $R^{14p}$ group in Formula P2, $R^{24p}$ group in Formula P3, and $R^{33p}$ and $R^{34p}$ group in Formula P4 are attached such that
  i) the carbon atom attached to the pyrrole ring is attached to three or four carbon atoms,
  ii) the carbon atom adjacent to the carbon atom attached to pyrrole ring is attached to three or four carbon atoms, or
  iii) the $C_3$ to $C_{45}$ silyl group has Formula Si1

wherein $R^{1s}$, $R^{2s}$, and $R^{3s}$ independently are a $C_1$ to $C_{15}$ hydrocarbyl group.

28. The process of claim 21, wherein:
a) the transition metal compound is chromium(III) 2-ethylhexanoate, chromium(III) octanoate, chromium(III) 2,2,6,6,-tetramethylheptanedionate, chromium(III) naphthenate, chromium(III) acetate, chromium(III) propionate, chromium(III) butyrate, chromium(III) neopentanoate, chromium(III) laurate, chromium(III) stearate, chromium(III) oxalate, chromium(II) bis(2-ethylhexanoate), chromium(II) acetate, chromium(II) propionate, chromium(II) butyrate, chromium(II) neopentanoate, chromium(II) laurate, chromium(II) stearate, chromium(II) oxalate, or a combination thereof;
b) the pyrrole compound is 2-methyl-4-isopropylpyrrole, 2-ethyl-4-isopropylpyrrole, 2-methyl-4-t-butylpyrrole, 2-ethyl-4-t-butylpyrrole, or a combination thereof; and
c) the metal alkyl is a trialkylaluminum compound, an alkylaluminum halide compound, or a combination thereof.

\* \* \* \* \*